US008921533B2

(12) United States Patent
Heyman et al.

(10) Patent No.: US 8,921,533 B2
(45) Date of Patent: Dec. 30, 2014

(54) GLYCOSYLATED VALPROIC ACID ANALOGS AND USES THEREOF

(75) Inventors: Norman S. Heyman, New York, NY (US); Brian K. Shull, Durham, NC (US)

(73) Assignee: Chromatin Technologies, New York, NY (US)

( * ) Notice: Subject to any disclaimer, the term of this patent is extended or adjusted under 35 U.S.C. 154(b) by 0 days.

(21) Appl. No.: 13/557,528

(22) Filed: Jul. 25, 2012

(65) Prior Publication Data

US 2013/0029924 A1  Jan. 31, 2013

Related U.S. Application Data

(60) Provisional application No. 61/511,219, filed on Jul. 25, 2011.

(51) Int. Cl.
*C07H 13/04* (2006.01)
*C07H 15/18* (2006.01)
*A61K 31/7028* (2006.01)

(52) U.S. Cl.
CPC ............ *A61K 31/7028* (2013.01); *C07H 13/04* (2013.01); *C07H 15/18* (2013.01)
USPC .......................................... 536/18.2; 514/25

(58) Field of Classification Search
CPC .................................. C07H 13/04; C07H 3/02
See application file for complete search history.

(56) References Cited

U.S. PATENT DOCUMENTS

| | | | |
|---|---|---|---|
| 5,162,573 A | 11/1992 | Chiesi et al. |
| 5,192,744 A | 3/1993 | Bouck et al. |
| 5,278,155 A | 1/1994 | Ikekawa et al. |
| 5,278,296 A | 1/1994 | Klemke |
| 5,369,108 A | 11/1994 | Breslow et al. |
| 5,426,100 A | 6/1995 | Deutch et al. |
| 5,453,500 A | 9/1995 | Koreeda et al. |
| 5,496,806 A | 3/1996 | Klemke |
| 5,672,746 A | 9/1997 | Nau et al. |
| 5,677,286 A | 10/1997 | Shull et al. |
| 5,693,767 A | 12/1997 | Klemke et al. |
| 5,700,811 A | 12/1997 | Breslow et al. |
| 5,733,876 A | 3/1998 | O'Reilly et al. |
| 5,840,692 A | 11/1998 | Deutch et al. |
| 5,854,205 A | 12/1998 | O'Reilly et al. |
| 5,932,616 A | 8/1999 | Breslow et al. |
| 5,932,709 A | 8/1999 | Shull et al. |
| 5,990,280 A | 11/1999 | Van Meir et al. |
| 5,994,292 A | 11/1999 | Tosato et al. |
| 6,087,367 A | 7/2000 | Breslow et al. |
| 6,093,805 A | 7/2000 | Shull et al. |
| 6,103,884 A | 8/2000 | Koreeda et al. |
| 6,169,076 B1 | 1/2001 | Shull et al. |
| 6,281,214 B1 | 8/2001 | Akasaka et al. |
| 6,281,229 B1 | 8/2001 | Yokota et al. |
| 6,316,436 B1 | 11/2001 | deSolms et al. |
| 6,342,219 B1 | 1/2002 | Thorpe et al. |
| 6,342,221 B1 | 1/2002 | Thorpe et al. |
| 6,346,510 B1 | 2/2002 | O'Reilly et al. |
| 6,358,956 B1 | 3/2002 | Hartman et al. |
| 6,387,903 B1 | 5/2002 | Dinsmore et al. |
| 6,462,182 B1 | 10/2002 | Tuinman et al. |
| 6,479,512 B1 | 11/2002 | Fraley et al. |
| 6,511,990 B1 | 1/2003 | Breslow et al. |
| 6,562,823 B1 | 5/2003 | Dinsmore et al. |
| 6,610,722 B2 | 8/2003 | Stump et al. |
| 6,613,780 B2 | 9/2003 | Yokota et al. |
| 6,719,540 B2 | 4/2004 | Regueiro-Ren et al. |
| 6,720,307 B2 | 4/2004 | Tuinman et al. |
| 6,794,392 B1 | 9/2004 | Suzuki et al. |
| 6,797,488 B1 | 9/2004 | Sukhatme |
| 6,849,599 B2 | 2/2005 | Calabresi et al. |
| 6,869,952 B2 | 3/2005 | Bhide et al. |
| 6,872,715 B2 | 3/2005 | Santi et al. |
| 6,887,874 B2 | 5/2005 | Hennequin |
| 6,890,917 B2 | 5/2005 | Snader et al. |
| 6,903,116 B2 | 6/2005 | Yokota et al. |
| 6,958,340 B2 | 10/2005 | Bilodeau et al. |
| 6,979,682 B2 | 12/2005 | Hunt et al. |
| RE39,754 E | 7/2007 | Suzuki et al. |
| 7,265,154 B2 | 9/2007 | Gottlicher et al. |
| 7,279,331 B2 | 10/2007 | Black et al. |
| RE40,703 E | 4/2009 | Suzuki et al. |
| 7,517,891 B2 | 4/2009 | Shull |
| 7,569,609 B2 | 8/2009 | Ohuchida et al. |
| 7,579,375 B2 | 8/2009 | Imawaka et al. |
| 2012/0295866 A1 | 11/2012 | Shull et al. |

FOREIGN PATENT DOCUMENTS

| | | |
|---|---|---|
| EP | 1158984 | 5/2000 |
| EP | 1170008 | 1/2002 |
| EP | 1324985 | 7/2003 |
| WO | WO-99/10329 | 3/1999 |

(Continued)

OTHER PUBLICATIONS

Redecker et al., Neuropharmacology, 2000, 39, p. 267-281.*
Armand et al., Epilepsy Research, 1995, 22, p. 185-192.*
Yamamura et al., Radioisotopes, 1999, 48, p. 383-389.*
Loscher, W., Prog. Neurobiol., 1999, 58, p. 31-59.*
Terui, Takeshi, et al., "Induction of *PIG3* and *NOXA* through Acetylation of p53 at 320 and 373 Lysine Residues as a Mechanism for Apoptotic Cell Death by Histone Deacetylase Inhibitors", *Cancer Res*, Dec. 24, 2003, vol. 63, pp. 8948-8954.
Kim, Tae Hyun, et al., "Efficacy on anaplastic thyroid carcinoma of valproic acid alone or in combination with doxorubicin, a synthetic chenodeoxychoclic acid derivative, or lactacystin", *Int. J. Oncol.*, 2009, vol. 34, No. 5, pp. 1353-1362.
Camphausen, Kevin, et al., "Enhancement of in vitro and in vivo tumor cell radiosensitivity by valproic acid", *Int. J. Cancer*, 2005, vol. 114, No. 3, pp. 380-386.
Chinnaiyan, Prakash, et al., "Postradiation Sensitization of the Histone Deacetylase Inhibitor Valproic Acid", *Clin. Cancer Res.* 2008, vol. 14, pp. 5410-5415.

(Continued)

*Primary Examiner* — Shaojia Anna Jiang
*Assistant Examiner* — Jonathan S Lau
(74) *Attorney, Agent, or Firm* — Wilmer Cutler Pickering Hale and Dorr LLP

(57) ABSTRACT

Glycosylated valproic acid and its analogs are provided. In some embodiments, the glycosylated valproic acid and its analogs have improved solubility and are ideal for drug delivery to treat a variety of diseases.

10 Claims, 3 Drawing Sheets

(56) References Cited

FOREIGN PATENT DOCUMENTS

| WO | WO-00/51614 | 9/2000 |
|----|-------------|--------|
| WO | WO-01/07046 | 2/2001 |
| WO | WO-01/51125 | 7/2001 |

OTHER PUBLICATIONS

Shein, Na'ama, et al., "Histone Deacetylase Inhibitors as Therapeutic Agents for Acute Central Nervouc System Injuries", *Mol. Med.* 2011, vol. 17, Nos. 5-6, pp. 448-456.

Peterson, Randall, et al., "Discovery and Use of Small Molecules for Probing Biological Processes in Zebrafish", *Methods in Cell Biol.* 2004, Chapter 26, vol. 76, pp. 569-591.

Bhavsar, Pankaj, et al., "The role of histone deacetylases in asthma and allergic diseases", *J. Allegy Clin. Immunol.*, Mar. 2008, vol. 121, pp. 580-584.

Adler, Joel T., et al., "Histone deacetylase inhibitors upregulate Notch-1 and inhibit growth in pheochromocytoma cells", *Surgery*, Dec. 2008, vol. 144, No. 6, pp. 956-962.

Hunter, Arwen L., et al. "Nonviral Reprogramming: Toward a Safer Induced Pluripotent Stem Cell", Advances in Wound Care, 2011, vol. 2, Ch. 4, pp. 21-25.

Huangfu, Danwei, et al., "Induction of pluripotent stem cells by defined factors is greatly improved by small-molecule compounds", *Nat Biotechnol.* 2008, vol. 26, No. 7, pp. 795-797.

Weinhold, Bob, et al., "Epigenetics: The Science of Change", *Environ Health Perspect*, Mar. 2006, vol. 114, No. 3, pp. A160-A167.

Mross, K., et al., "A phase I clinical and pharmacokinetic study of the camptothecin glycoconjugate, BAY 38-3441, as a daily infusion in patients with advanced solid tumors", *Annals of Oncology*, 2004, vol. 15, pp. 1284-1294.

Ishihar, K. et al., "An Extremely Simple, Convenient, and Selective Method for Acetylating Primary Alcohols in the Presence of Secondary Alcohols", *J. Org. Chem.*, 1993, vol. 58, pp. 3791-3793.

Kawabata, Takeo, et al., "A Catalytic One-Step Process for the Chemo- and Regioselective Acylation of Monosaccharides", *J. Am. Chem. Soc.*, Sep. 29, 2007, vol. 129, pp. 12890-12895.

ard, Peter J., et al., "Fluorinated carbohydrates. 2. Selective fluorination of gluco- and mannopyranosides. Use of 2-D NMR for structural assignments", *J. Org. Chem.*, 1983, vol. 48, pp. 4734-4743.

Gemma, Emiliano, et al., "Synthesis of the tetrasaccharide α-d-Glcp-(1-3)-•α-d-Manp-(1-2)-•α-d-Manp-(1-2)-•α-d-Manp recognized by Calreticulin/Calnexin", *Carbohydr. Res.*, 2005, vol. 340, pp. 2558-2562.

Lee, Doris, et al., "Boronic Acid-Catalyzed Regioselective Acylation of Carbohydrate Derivatives", *J. Am. Chem. Soc.*, 2011, vol. 133, pp. 3724-3727.

Witschi, Mark. A., et al., "Selective Acetylation of per-O-TMS-Protected Monosaccharides", *Org. Lett.*, 2010, vol. 12, No. 19, pp. 4312-4315.

Björkling, Fredrik, et al., "A Highly Selective Enzyme-catalysed Esterification of Simple Glucosides", *J. Chem. Soc., Chem. Comm.*, 1989, pp. 934-935.

Dash, Pramod K., et al., "Valproate Administered after Traumatic Brain Injury Provides Neuroprotection and Improves Cognifitive Function in Rats", PLoS ONE, Jun. 2010, vol. 5, No. 6, pp. 1-13.

Bowkett, Elizabeth R. et al., "Efficient synthesis of 1β-O-acyl gluuronides via selective acylation of allyl or benzyl $_D$-glucuronate," Tetrahedron, vol. 63, No. 32, pp. 7596-7605 (May 17, 2007).

Katsnelson, Alla, "Setback prompts rethink of latency-reversing strategy to eliminate HIV infection," Nature Reviews, vol. 13, pp. 403-404 (Jun. 2014).

Kawai, Satoshi et al., "Determination of 3-Keto-valproate in Urine by Metal Capillary Gas Chromatography," Analytical Sciences, vol. 5, No. 3, pp. 301-304 (Jun. 1989).

Van Breemen, Richard B. et al., "Characterization of Acyl-linked Glucuronides by Electron Impact and Fast Atom Bombardment Mass Spectrometry," Biomedical and Environmental Mass Spectrometry, vol. 17, No. 2, pp. 97-103 (Feb. 22, 1988).

Yamamura, Naotoshi et al., "High-yield Enzymatic Synthesis of $14_C$- or $3_H$-Labeled 1-O-Valproyl-β-D-glucopyranuronic Acid, the Main Metabolite of Valproic Acid in Human," Radioisotopes, vol. 48, No. 6, pp. 383-389 (Jan. 18, 1999).

Yokogawa, Koichi et al., "Effect of Meropenem on Disposition Kinetics of Valproate and Its Metabolites in Rabbits," Pharmaceutical Research, vol. 18, No. 9, pp. 1320-1326 (Sep. 2001).

\* cited by examiner

GLYCOSYLATED VALPROIC ACID ANALOGS AND USES THEREOF

This application claims priority to U.S. Provisional Application No. 61/511,219, filed on Jul. 25, 2011, the entirety of which is incorporated herein by reference.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

TECHNICAL FIELD

This application relates to glycosylated valproic acid and its analogs.

BACKGROUND OF THE INVENTION

Valproic acid is a carboxylic acid that has been used to treat epilepsy and other CNS disorders such as manic episodes in bipolar disorder and in migraine headaches. More recent research has shown it to be a strong histone deacetylase (HDAC) Class 1 epigenetic inhibitor. HDACs are chromatin remodeling factors that normally help condense DNA into its compact form. When chromatin is in its compacted form, transcription or other factors cannot access DNA and viruses that infect cells such as HIV stay bound and hidden, eluding the attack of anti-viral therapy. HDAC inhibitors including valproic acid are thought to transform the chromatin in the latently infected cell from its condensed (or transcriptional silent) form to its less condensed (or transcriptional active) form. HDAC inhibitors also have implications in stem cell proliferation and reprogramming of adult stem cells.

U.S. Pat. No. 5,162,573 describes 2-propyl-2-pentanoic acid (valproic acid) esters of formula (I):

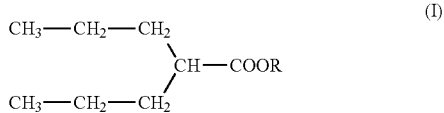

and (E)-2-propyl-2-pentenoic acid (E)-2-valproenoic acid esters of formula (II)

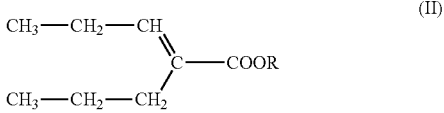

wherein R is an alkoxyalkyl, alkanoyloxyalkyl, aroyloxyalkyl, alkoxycarbonyloxyalkyl, aralkenoyloxyalkyl group, a mono- or bicyclic heterocycloalkyl group, which may be saturated or unsaturated and optionally substituted with a $C_1$-$C_4$ alkyl group or an oxo group; the above cited alkyl, alkoxyl and alkanoyl groups having straight or branched chain and containing 1 to 10 carbon atoms.

In formulae I and II of U.S. Pat. No. 5,162,573, R preferably represents 2-methoxyethyl, 2-isopropoxyethyl, 2-butoxyethyl, 1-methyl-2-methoxyethyl, acetoxymethyl, 2-acetoxyethyl, pivaloyloxymethyl, 1- and 2-pivaloyloxyethyl, 2-propyl-pentanoyloxymethyl, 2-propyl-pentenoyloxymethyl, 2-(2-propylpentanoyloxy)ethyl, 2-(2-propyl-pentenoyloxy)ethyl, 1-ethoxycarbonyloxyethyl, 2-benzoyloxyethyl, 2-(3,4,5-trimethoxylbenzoyloxy)ethyl, 2-cinnamoyloxyethyl, 2-phthalidyl, 2-(N-succinimido)ethyl, (5-methyl-2-oxo-1,3-dioxolene-4-yl)methyl, 2-pyridylmethyl.

U.S. Pat. No. 7,579,375 discloses compounds of the formula

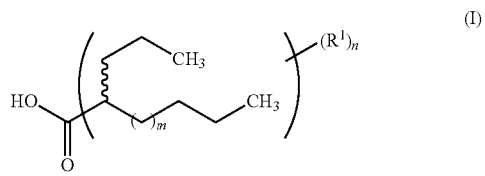

wherein $R^1$ represents optionally protected hydroxy or oxo, ⁓ indicates R-configuration, S-configuration or a mixture of these in an arbitrary proportion,
n represents an integer of 1 to 3, and
m represents 0 or an integer of 1 to 10; and
wherein two or more $R^1$'s are not bound to the same carbon atom other than the terminal carbon atom,
a salt thereof or a prodrug thereof. In some embodiments, the compound can have a metal.

U.S. Pat. No. 7,569,609 describes compounds of the formula (I):

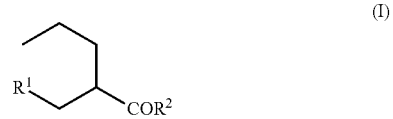

wherein $R^1$ is $C_{1-10}$ alkyl having one carbon substituted by 1-3 of fluorine(s); $R^2$ is hydroxy, $C_{1-4}$ alkoxy, $C_{1-4}$ alkoxy substituted by 1 of phenyl, or $NR^3R^4$, in which $R^3$ and $R^4$ each, independently, is (i) hydrogen, (ii) $C_{1-4}$ alkyl, (iii) phenyl, (iv) phenyl substituted by $C_{1-4}$ alkoxy or carboxyl, (v) 4-7 membered heterocyclic ring containing one nitrogen or (vi) $C_{1-4}$ alkyl substituted by phenyl, phenyl substituted by $C_{1-4}$ alkoxy or carboxyl, or 4-7 membered heterocyclic ring containing one nitrogen, or the nitrogen atom bonded to them, taken together is 4-7 membered saturated heterocyclic ring containing one or two nitrogen(s) or one nitrogen and one oxygen, or amino acid residue; with the proviso that, $R^1$ is not F—$(CH_2)_4$—, F—$(CH_2)_5$—, F—$(CH_2)_6$—, $F_3C$—$CH_2$—; and non-toxic salts thereof and acid addition salts thereof,
and compounds of formula (X):

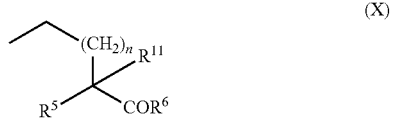

wherein n is 0 or 1; $R^{11}$ is hydrogen or chlorine; $R^5$ is $R^7$—$CH_2$— or $R^8$, or $R^5$ and $R^{11}$, taken together is $C_{3-10}$ alkylidene; $R^7$ is F—$(CH_2)_m$—, in which m is 4-6, $F_3C$—$CH_2$—, $C_{2-10}$ alkyl substituted by 1 or 2 of chlorine(s), or $C_{1-5}$ alkyl substituted by 1 or 2 of $C_{1-4}$alkoxy, $C_{3-7}$ cycloalkyl, phenyl or phenoxy; $R^8$ is (i) $C_{3-10}$ alkyl (ii) $C_{3-10}$ alkenyl, (iii)

$C_{2-10}$ alkoxy, (iv) $C_{2-10}$ alkylthio, (v) $C_{3-7}$ cycloalkyl, (vi) phenyl or (vii) phenoxy; $R^6$ is hydroxy, $C_{1-4}$alkoxy, $C_{1-4}$ alkoxy substituted by 1 of phenyl, or $NR^9R^{10}$, in which $R^9$ and $R^{16}$ each, independently, is (i) hydrogen, (ii) $C_{1-4}$ alkyl, (iii) phenyl, (iv) phenyl substituted by $C_{1-4}$ alkoxy or carboxyl, (v) 4-7 membered heterocyclic ring containing one nitrogen or (vi) $C_{1-4}$ alkyl substituted by phenyl, phenyl substituted by $C_{1-4}$alkoxy or carboxyl, or 4-7 membered heterocyclic ring containing one nitrogen, or the nitrogen atom bonded to them, taken together is 4-7 membered saturated heterocyclic ring containing one or two nitrogen(s) or one nitrogen and one oxygen, or amino acid residue; non-toxic salts thereof and acid addition salts thereof.

U.S. Pat. No. 5,672,746 describes compounds of formula

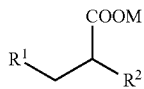

wherein $R^1$ is —C≡CH, —CH=CH$_2$, or —CH$_2$—CH$_3$,
M is a hydrogen or a metal atom;
$R^2$ is independently a saturated, unsaturated with at least one double or triple bond, branched or unbranched $C_{1-30}$ alkyl group, optionally substituted with an aliphatic or aromatic $C_{3-9}$cyclohydrocarbon or heterocyclic group; with the proviso that when $R^1$ is CH$_2$—CH$_3$, $R^2$ is $C_{5-30}$, and that formula I is not 2-n-propyl-4-pentynoic acid or 2-n-propyl-4-pentenoic acid (4-en-VPA).

Despite the potential utility of valproic acid and it analogs as an HDAC inhibitor, low solubility of the carboxylic acid compounds limit application of these compounds. Thus, there is still a need for the development of new valproic acid analogs that will allow the production of better formulations that can easily be administered to the patient.

SUMMARY OF THE INVENTION

In one aspect of the invention, new valproic acid analogs are provided. In some embodiments, glycosylated valproic acid and its analogs are provided that have improved solubility and membrane transport as the sugar moiety of the molecule is believed to enhance solubility and/or transport into cells. In some embodiments, the valproic acid analogs allow the production of better formulations and/or easier administration.

In one aspect, there is a compound of formula I, II, III, IV, V, or VI:

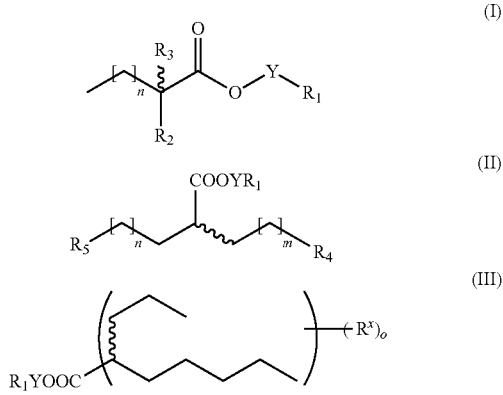

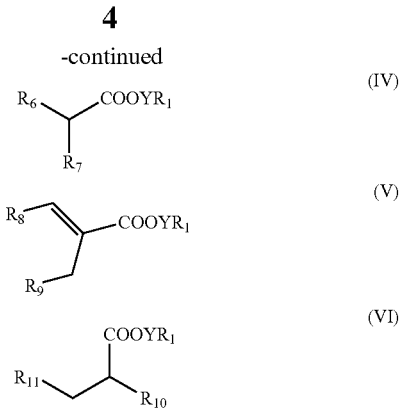

wherein
$R_1$ is saccharide;
$R_2$ is $C_{1-10}$ alkyl or alkene having one carbon substituted by 1-3 halogen atoms, amino, hydroxy, carboxylic acid group, ester, amide, or cyano, wherein one or more of the hydroxy, carboxylic acid or amide group is optionally glycosylated with a saccharide group;
$R_3$ is H, halo or loweralkyl;
each $R_4$ and $R_5$ is independently amine, amide, thiol, cyano, hydroxyl, or carboxylic acid, each of which may be glycosylated;
$R^x$ is oxo or hydroxy;
each of $R_6$ and $R_7$ is a linear or branched, saturated or partially unsaturated aliphatic $C_2$-$C_{20}$ hydrocarbon chain;
each of $R_8$ and $R_9$ is a linear or branched aliphatic $C_2$-$C_{20}$ hydrocarbon chain which is optionally substituted with a $C_3$-$C_9$ aliphatic or aromatic cyclohydrocarbon or heterocyclic group or having 1-3 substituents independently selected from the group consisting of halogen atoms, amino, hydroxy, carboxylic acid group, ester, amide, and cyano, wherein one or more of the hydroxy, carboxylic acid, amine, and amide group is optionally glycosylated with a saccharide group;
$R_{10}$ is —C≡CH, —CH=CH$_2$, or —CH$_2$—CH$_3$;
$R_{11}$ is independently a saturated, unsaturated with at least one double or triple bond, branched or unbranched $C_{1-30}$ alkyl group, optionally substituted with an aliphatic or aromatic $C_{3-9}$ cyclohydrocarbon or heterocyclic group;
Y is a bond or —CH$_2$-aryl-O—, wherein the aryl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl) ($C_1$-$C_3$ alkyl), —NH($C_1$-$C_3$ alkyl), —NH$_2$, —NO$_2$, and —CN;
each of m and n is independently an integer having a value of 0, 1, 2, 3, 4, 5, or 6; and
o is 1, 2, or 3;
or a pharmaceutically acceptable salt or prodrug thereof.

In some embodiments, the compound comprises a sugar that is in a furanose and/or a pyranose form. In some embodiments, the sugar of the compound comprises glucose, mannose, galactose, 2-NAc glucose, or 2-deoxyglucose. In some embodiments, the sugar can be monosaccharide, disaccharide, or trisaccharide analogs. In some embodiments, the compound exhibits glycosylation at the C-1 and/or C-6 positions. In some embodiments, the compound comprises an alpha and beta anomer for one or more C-1 analogs.

In another aspect, there is a method of treating, ameliorating, or preventing viral infections comprising administering to an animal in need thereof a therapeutically effective amount of the glycosylated valproic acid or its analogs. In some embodiments, the glycosylated valproic acid or analogs comprise a compound of formulae (I)-(VI).

In some embodiments, the glycosylated valproic acid or its analogs can be used to treat a viral infection (e.g., such as HIV) or cancer. Some types of cancers that the glycosylated valproic acid or its analogs can treat include colon cancer, brain cancer, glioma, multiple myeloma, head and neck cancer, hepatocellular cancer, melanoma, ovarian cancer, cervical cancer, renal cancer, and non-small cell lung cancer. In some embodiments, the cancer is acute and chronic lymphocytic leukemia, acute granulocytic leukemia, adrenal cortex carcinoma, bladder carcinoma, breast carcinoma, cervical carcinoma, cervical hyperplasia, choriocarcinoma, chronic granulocytic leukemia, chronic lymphocytic leukemia, colon carcinoma, endometrial carcinoma, esophageal carcinoma, essential thrombocytosis, genitourinary carcinoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, osteogenic sarcoma, ovarian carcinoma, pancreatic carcinoma, polycythemia vera, primary brain carcinoma, primary macroglobulinemia, prostatic carcinoma, renal cell carcinoma, rhabdomyosarcoma, skin cancer, small-cell lung carcinoma, soft-tissue sarcoma, squamous cell carcinoma, stomach carcinoma, testicular carcinoma, thyroid carcinoma, or Wilms' tumor of the kidney.

In some embodiments, the glycosylated valproic acid and its analogs provided have a sugar attached thereto. In some embodiments, the compounds reduce and/or prevent drug resistance that may develop over time.

In some embodiments, the glycosylated valproic acid and its analogs provided can be used in both reprogramming of adult cells to the totipotent state and further on to other adult cells, and in stem cell proliferation in the rate of growth of those cells. Therefore, the glycosylated valproic acid and its analogs can be used as a tool in organ regeneration, and improving the rate of cell proliferation.

In some embodiments, the glycosylated valproic acid and its analogs provided can be used in combination with gene therapy.

Additional features and advantages of various aspects and embodiments will be set forth in part in the description that follows, and in part will be apparent from the description, or may be learned by practice of various aspects and embodiments. The objectives and other advantages of various aspects and embodiments will be realized and attained by means of the elements and combinations particularly pointed out in the description and appended claims.

These and other embodiments of the invention are further described in the following sections of the application, including the Detailed Description, Examples, and Claims. Still other objects and advantages of the invention will become apparent by those of skill in the art from the disclosure herein, which are simply illustrative and not restrictive. Thus, other embodiments will be recognized by the ordinarily skilled artisan without departing from the spirit and scope of the invention.

BRIEF DESCRIPTION OF THE FIGURES

The following figures are illustrative only and not intended to be limiting.

DETAILED DESCRIPTION OF THE INVENTION

Figure 1:
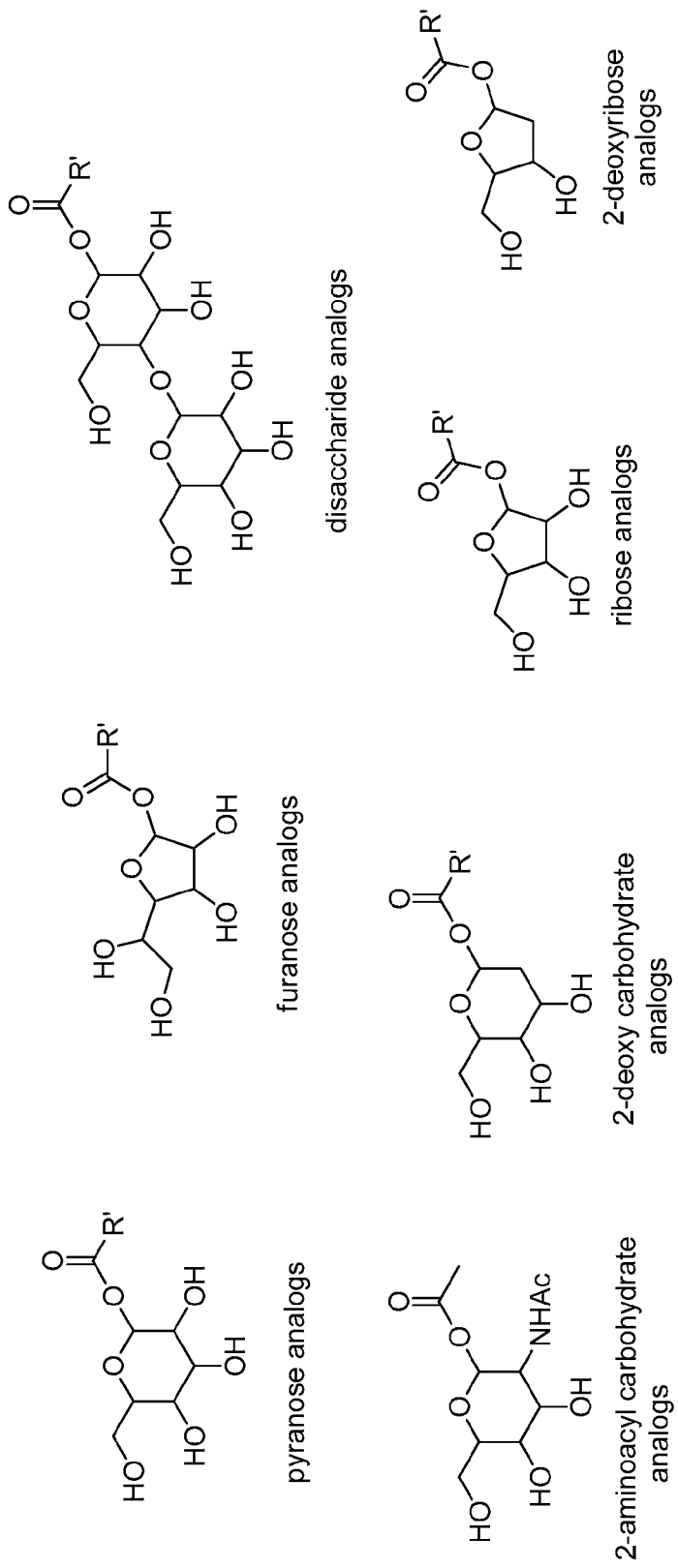
FIG. 1 shows representative glycosylated analogs linked at C-1 of the sugar.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "an analog" includes one, two, three or more analogs.

The present invention relates to compounds, processes of preparing them and methods of using the compounds.

In some embodiments, the present invention relates to compounds of formula I:

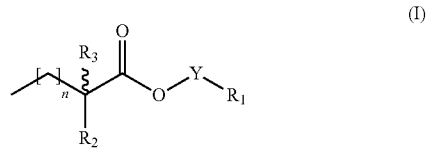

(I)

wherein, $R_1$ is saccharide;

$R_2$ is $C_{1-10}$ alkyl or alkene having 1-3 substituents independently selected from the group consisting of halogen atoms, amino, hydroxy, carboxylic acid group, ester, amide, and cyano, wherein one or more of the hydroxy, carboxylic acid, amine, or amide group is optionally glycosylated with a saccharide group;

$R_3$ is H, halo or lower alkyl;

Y is a bond or —CH$_2$-aryl-O—, wherein the aryl group is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy, C$_1$-C$_6$ thioalkyl, —N(C$_1$-C$_3$ alkyl)(C$_1$-C$_3$ alkyl), —NH(C$_1$-C$_3$ alkyl), —NH$_2$, —NO$_2$, and —CN; and n is an integer having a value of 0, 1, 2, 3, 4, 5, or 6; or pharmaceutically acceptable acid addition salts thereof.

In some embodiments, the invention is drawn to compounds of formula II:

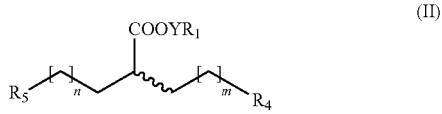

(II)

wherein R$_1$ and Y are as defined above and each R$_4$ and R$_5$ is independently amine, cyano, hydroxyl, or carboxylic acid, each of which may be glycosylated; each of m and n is an integer having a value of 0, 1, 2, 3, 4, 5, or 6; and pharmaceutically acceptable acid addition salts or prodrugs thereof.

In some embodiments, the invention is drawn to compounds of formula III:

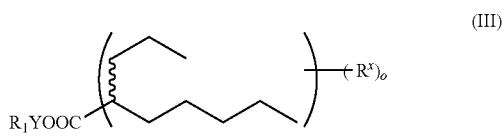

(III)

wherein R$_1$ and Y are as defined above; R$^x$ is oxo or hydroxy; o is 1, 2, or 3; and pharmaceutically acceptable acid addition salts or prodrugs thereof. In certain embodiments, Rx is a glycosylated hydroxy group.

In some embodiments, the invention is drawn to compounds of formula IV:

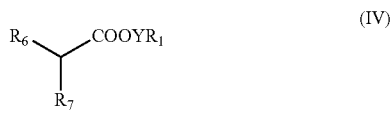

(IV)

wherein R$_1$ and Y are as defined above; each of R$_6$ and R$_7$ is a linear or branched, saturated or partially unsaturated aliphatic C$_2$-C$_{20}$ hydrocarbon chain. Examples of hydrocarbon chains include alkyl, alkenyl, and alkynyl. The hydrocarbon chain may be substituted with a carbocycle or a heterocycle. In some embodiments, R$_6$ is —CH$_2$C≡CH, —CH$_2$CH═CH$_2$, or —CH$_2$CH$_2$CH$_3$ and R$_7$ is a saturated, unsaturated, branched or unbranched C$_1$-C$_{20}$ alkyl group which is optionally substituted with a C$_3$-C$_9$ aliphatic or aromatic cyclohydrocarbon or heterocyclic group. In certain embodiments, R$_6$ and R$_7$ may comprise one or more heteroatoms selected from the group consisting oxygen, nitrogen and sulfur, replacing carbon atoms in the hydrocarbon chain. In certain embodiments, R$_6$ and R$_7$ independently comprise 2 to 10, more preferably 3 to 10 or 5 to 10 carbon atoms. In certain embodiments, R$_6$ and R$_7$ independently are saturated or comprise one double bond or one triple bond. In particular, one of R$_6$ and R$_7$ may contain a double or a triple bond in position 2 and 3 of the chain or heteroatoms which generate a similar structure. R$_6$ or R$_7$ may include one or more aromatic rings or heterocycles, and yet inhibit HDAC activity because the catalytic site of the HDAC protein apparently accommodates a wide variety of binding molecules. In particular embodiments, compound of formula IV may contain a propinyl residue as one of R$_6$ or R$_7$ and residues of seven or more carbons as the other of R$_6$ and R$_7$.

In some embodiments, the invention is drawn to compounds of formula V:

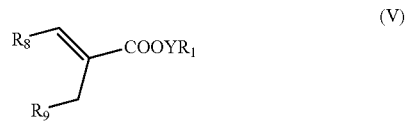

(V)

wherein R$_1$ and Y are as defined above; each of R$_8$ and R$_9$ is a linear or branched aliphatic C$_2$-C$_{20}$ hydrocarbon chain which is optionally substituted with a C$_3$-C$_9$ aliphatic or aromatic cyclohydrocarbon or heterocyclic group or having 1-3 substituents independently selected from the group consisting of halogen atoms, amino, hydroxy, carboxylic acid group, ester, amide, and cyano, wherein one or more of the hydroxy, carboxylic acid, amine, or amide group is optionally glycosylated with a saccharide group.

In some embodiments, the invention is drawn to compounds of formula VI:

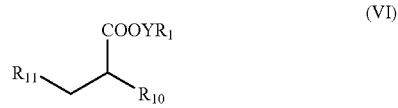

(VI)

wherein R$_1$ and Y are as defined above or a group I metal; R$_{10}$ is —C≡CH, —CH═CH$_2$, or —CH$_2$—CH$_3$; and R$_{11}$ is independently a saturated, unsaturated with at least one double or triple bond, branched or unbranched C$_{1-30}$ alkyl group, optionally substituted with an aliphatic or aromatic C$_{3-9}$ cyclohydrocarbon or heterocyclic group.

In some embodiments, the compound comprises a saccharide that is a furanose or a pyranose. In some embodiments, the saccharide is a furanose. In some embodiments, the saccharide is a pyranose.

In some embodiments, the compound comprises a saccharide that comprises glucose, mannose, galactose, 2-NAc glucose, or 2-deoxyglucose. In some embodiments, the saccharide comprises glucose, mannose, or galactose. In some embodiments, the saccharide comprises 2-NAc glucose or 2-deoxyglucose. In some embodiments, the saccharide comprises glucose. In some embodiments, the saccharide comprises mannose. In some embodiments, the saccharide comprises galactose. In some embodiments, the saccharide comprises 2-NAc glucose. In some embodiments, the saccharide comprises 2-deoxyglucose.

In some embodiments, the compound comprises a saccharide that comprises a ribose, or 2-deoxyribose.

In some embodiments, the saccharide is a monosaccharide, disaccharide, trisaccharide or analog thereof. In some embodiments, the saccharide is a monosaccharide, disaccharide, or analog thereof. In some embodiments, the saccharide is a monosaccharide or analog thereof. In some embodiments, the saccharide is a monosaccharide. In some embodiments, the saccharide is a disaccharide or analog thereof. In some embodiments, the saccharide is a disaccharide. In some embodiments, the disaccharide is lactose. In some embodiments, the disaccharide is maltose. In some embodiments, the saccharide is a trisaccharide or analog thereof. In some embodiments, the saccharide is a trisaccharide.

In some embodiments, the compound exhibits glycosylation at C-1 and/or C-6 positions of the saccharide. In some embodiments, the compound exhibits glycosylation at C-1 position of the saccharide. In some embodiments, the compound exhibits glycosylation at C-6 position of the saccharide.

In some embodiments, the compound comprises an alpha and beta anomer at the C-1 position of the saccharide. In some embodiments, the compound comprises an alpha anomer at the C-1 position of the saccharide. In some embodiments, the compound comprises a beta anomer at the C-1 position of the saccharide.

In some embodiments, $R_1$ is a furanose or a pyranose. In some embodiments, the $R_1$ is a furanose. In some embodiments, $R_1$ is a pyranose.

In some embodiments, $R_1$ is a glucose, mannose, galactose, 2-NAc glucose, or 2-deoxyglucose. In some embodiments, $R_1$ is glucose, mannose, or galactose. In some embodiments, $R_1$ is 2-NAc glucose or 2-deoxyglucose. In some embodiments, $R_1$ is glucose. In some embodiments, $R_1$ is mannose. In some embodiments, $R_1$ is galactose. In some embodiments, $R_1$ is 2-NAc glucose. In some embodiments, $R_1$ is 2-deoxyglucose.

In some embodiments, $R_1$ is comprises a ribose, or 2-deoxyribose. In some embodiments, $R_1$ is ribose, or 2-deoxyribose. In some embodiments, $R_1$ is ribose. In some embodiments, $R_1$ is 2-deoxyribose.

In some embodiments, $R_2$ is $C_{1-10}$ alkyl or alkene having 1-3 substituents independently selected from the group consisting of halogen atoms, amino, hydroxy, carboxylic acid group, ester, amide, and cyano, wherein one or more of the hydroxy, carboxylic acid, amine, or amide group is optionally glycosylated with a saccharide group.

In some embodiments, $R_2$ is $C_{1-10}$ alkyl or alkene having 1-3 substituents independently selected from the group consisting of halogen atoms, amino, hydroxy, carboxylic acid group, ester, amide, and cyano.

In some embodiments, $R_2$ is $C_{1-10}$ alkyl or alkene having 1-3 substituents independently selected from the group consisting of halogen atoms, amino, hydroxy, carboxylic acid group, ester, and amide.

In some embodiments, $R_2$ is $C_{1-10}$ alkyl or alkene having 1-3 substituents independently selected from the group consisting of halogen atoms, amino, hydroxy, carboxylic acid group, ester, and amide.

In some embodiments, $R_2$ is $C_{1-8}$ alkyl or alkene having 1-3 substituents independently selected from the group consisting of halogen atoms, amino, hydroxy, ester, and amide.

In some embodiments, $R_2$ is $C_{1-6}$ alkyl or alkene having 1-3 substituents independently selected from the group consisting of halogen atoms or hydroxy.

In some embodiments, $R_2$ is $C_{1-4}$ alkyl or alkene having 1-3 substituents independently selected from the group consisting of halogen atoms or hydroxy.

In some embodiments, $R_2$ is $C_{1-10}$ alkyl or alkene. In some embodiments, $R_2$ is $C_{1-8}$ alkyl or alkene. In some embodiments, $R_2$ is $C_{1-6}$ alkyl or alkene. In some embodiments, $R_2$ is $C_{1-4}$ alkyl or alkene. In some embodiments, $R_2$ is $C_{1-4}$ alkyl. In some embodiments, $R_2$ is methyl, ethyl, or propyl. In some embodiments, $R_2$ is ethyl, or propyl. In some embodiments, $R_2$ is propyl.

In some embodiments, $R_3$ is H, halo or loweralkyl. In some embodiments, $R_3$ is H, or loweralkyl. In some embodiments, $R_3$ is H or $C_{1-4}$ alkyl. In some embodiments, $R_3$ is H or methyl. In some embodiments, $R_3$ is H.

In some embodiments, each $R_4$ and $R_5$ is independently amine, cyano, hydroxyl, or carboxylic acid each of which may be glycosylated. In some embodiments, each $R_4$ and $R_5$ is independently amine, cyano, hydroxyl, or carboxylic acid. In some embodiments, each $R_4$ and $R_5$ is independently amine, hydroxyl, or carboxylic acid. In some embodiments, each $R_4$ and $R_5$ is independently amine or hydroxyl. In some embodiments, each $R_4$ and $R_5$ is amine. In some embodiments, each $R_4$ and $R_5$ is hydroxyl.

In some embodiments, $R^x$ is oxo or hydroxyl. In some embodiments, $R^x$ is oxo. In some embodiments, $R^x$ is hydroxyl.

In some embodiments, each of $R_6$ and $R_7$ is independently a linear or branched, saturated or partially unsaturated aliphatic $C_2$-$C_{20}$ hydrocarbon chain. In some embodiments, each of $R_6$ and $R_7$ is independently a linear or branched, saturated or partially unsaturated aliphatic $C_2$-$C_{10}$ hydrocarbon chain. In some embodiments, each of $R_6$ and $R_7$ is independently a linear or branched, saturated aliphatic $C_2$-$C_{20}$ hydrocarbon chain. In some embodiments, each of $R_6$ and $R_7$ is independently a linear or branched, saturated aliphatic $C_2$-$C_{10}$ hydrocarbon chain. In some embodiments, each of $R_6$ and $R_7$ is independently a linear or branched, saturated aliphatic $C_2$-$C_6$ hydrocarbon chain. In some embodiments, each of $R_6$ and $R_7$ is independently a linear, saturated aliphatic $C_2$-$C_6$ hydrocarbon chain. In some embodiments, each of $R_6$ and $R_7$ is independently ethyl, propyl, butyl or pentyl. In some embodiments, each of $R_6$ and $R_7$ is independently ethyl, propyl, or butyl. In some embodiments, each of $R_6$ and $R_7$ is independently propyl or butyl. In some embodiments, each of $R_6$ and $R_7$ is independently propyl. In some embodiments, each of $R_6$ and $R_7$ is independently butyl.

In some embodiments, each of $R_8$ and $R_9$ is a linear or branched aliphatic $C_2$-$C_{20}$ hydrocarbon chain, which is optionally substituted with a $C_3$-$C_9$ aliphatic or aromatic cyclohydrocarbon or heterocyclic group or having 1-3 substituents independently selected from the group consisting of halogen atoms, amino, hydroxy, carboxylic acid group, ester, amide, and cyano.

In some embodiments, each of $R_8$ and $R_9$ is a linear or branched aliphatic $C_2$-$C_{20}$ hydrocarbon chain, having 1-3 substituents independently selected from the group consisting of halogen atoms, amino, hydroxy, carboxylic acid group, ester, amide, and cyano.

In some embodiments, each of $R_8$ and $R_9$ is a linear or branched aliphatic $C_2$-$C_{20}$ hydrocarbon chain, which is substituted with a $C_3$-$C_9$ aliphatic or aromatic cyclohydrocarbon or heterocyclic group.

In some embodiments, each of $R_8$ and $R_9$ is a linear or branched aliphatic $C_2$-$C_{10}$ hydrocarbon chain, which is optionally substituted with a $C_3$-$C_9$ aliphatic or aromatic cyclohydrocarbon or heterocyclic group or having 1-3 substituents independently selected from the group consisting of halogen atoms, amino, hydroxy, carboxylic acid group, ester, amide, and cyano.

In some embodiments, each of $R_8$ and $R_9$ is a linear or branched aliphatic $C_2$-$C_{10}$ hydrocarbon chain, which is substituted with a $C_3$-$C_9$ aliphatic or aromatic cyclohydrocarbon or heterocyclic group.

In some embodiments, each of $R_8$ and $R_9$ is a linear or branched aliphatic $C_2$-$C_{10}$ hydrocarbon chain, having 1-3 substituents independently selected from the group consisting of halogen atoms, amino, hydroxy, carboxylic acid group, ester, amide, and cyano.

In some embodiments, each of $R_8$ and $R_9$ is a linear or branched aliphatic $C_2$-$C_{10}$ hydrocarbon chain. In some embodiments, each of $R_8$ and $R_9$ is a linear or branched aliphatic $C_2$-$C_8$ hydrocarbon chain. In some embodiments, each of $R_8$ and $R_9$ is a linear aliphatic $C_2$-$C_{10}$ hydrocarbon chain. In some embodiments, each of $R_8$ and $R_9$ is ethyl, propyl, butyl, pentyl or hexyl. In some embodiments, each of $R_8$ and $R_9$ is ethyl, propyl, or butyl. In some embodiments, each of $R_8$ and $R_9$ is ethyl or propyl. In some embodiments, each of $R_8$ and $R_9$ is ethyl. In some embodiments, each of $R_8$ and $R_9$ is propyl.

In some embodiments, $R_{10}$ is —C≡CH, —CH=$CH_2$, or —$CH_2$—$CH_3$. In some embodiments, $R_{10}$ is —CH=$CH_2$ or —$CH_2$—$CH_3$. In some embodiments, $R_{10}$ is —C≡CH. In some embodiments, $R_{10}$ is —CH=$CH_2$. In some embodiments, $R_{10}$ is —$CH_2$—$CH_3$.

In some embodiments, $R_{11}$ is independently a saturated, unsaturated with at least one double or triple bond, branched or unbranched $C_{1-30}$ alkyl group, optionally substituted with an aliphatic or aromatic $C_{3-9}$ cyclohydrocarbon or heterocyclic group. In some embodiments, $R_{11}$ is independently a saturated, unsaturated with at least one double or triple bond, branched or unbranched $C_{1-30}$ alkyl group, optionally substituted with an aliphatic or aromatic $C_{3-9}$ cyclohydrocarbon or heterocyclic group.

In some embodiments, Y is a bond or —$CH_2$-aryl-O—, wherein the aryl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —$NH_2$, —$NO_2$, and —CN.

In some embodiments, Y is a bond or —$CH_2$-phenyl-O—, wherein the phenyl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —$NH_2$, —$NO_2$, and —CN.

In some embodiments, Y is a bond,

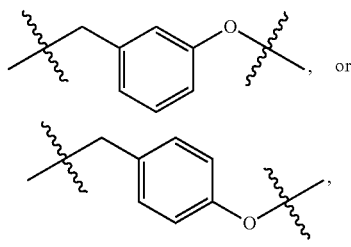, or

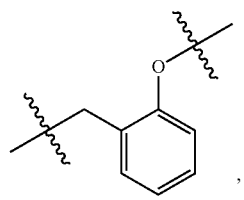 [SMILES: *Cc1ccccc1O*], wherein the phenyl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —$NH_2$, —$NO_2$, and —CN.

In some embodiments, Y is a bond,

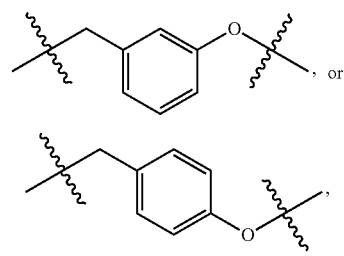, or wherein the phenyl group is optionally substituted with one or more substituents independently selected from $C_1$-$C_3$ alkyl, $C_1$-$C_3$ haloalkyl, $C_1$-$C_3$ alkoxy, $C_1$-$C_3$ haloalkoxy, $C_1$-$C_3$ thioalkyl, —N($C_1$-$C_3$ alkyl)($C_1$-$C_3$ alkyl), —NH($C_1$-$C_3$ alkyl), —$NH_2$, —$NO_2$, and —CN.

In some embodiments, Y is a bond,

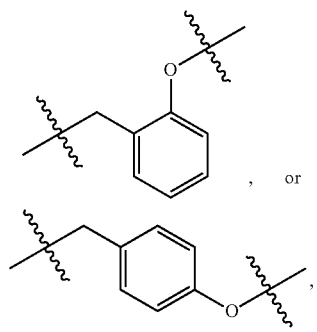, wherein the phenyl group is optionally substituted with one or more substituents independently selected from $C_1$-$C_3$ alkyl, $C_1$-$C_3$ haloalkyl, $C_1$-$C_3$ alkoxy, $C_1$-$C_3$ haloalkoxy, $C_1$-$C_3$ thioalkyl, —N($C_1$-$C_3$ alkyl)($C_1$-$C_3$ alkyl), —NH($C_1$-$C_3$ alkyl), —$NH_2$, —$NO_2$, and —CN.

In some embodiments, Y is a

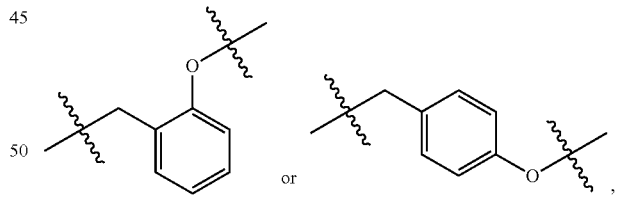

wherein the phenyl group is optionally substituted with one or more substituents independently selected from $C_1$-$C_3$ alkyl, $C_1$-$C_3$ haloalkyl, $C_1$-$C_3$ alkoxy, $C_1$-$C_3$ haloalkoxy, $C_1$-$C_3$ thioalkyl, —N($C_1$-$C_3$ alkyl)($C_1$-$C_3$ alkyl), —NH($C_1$-$C_3$ alkyl), —$NH_2$, —$NO_2$, and —CN.

In some embodiments, Y is a bond,

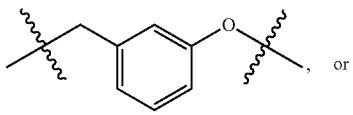, or

-continued

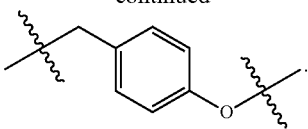

In some embodiments, Y is

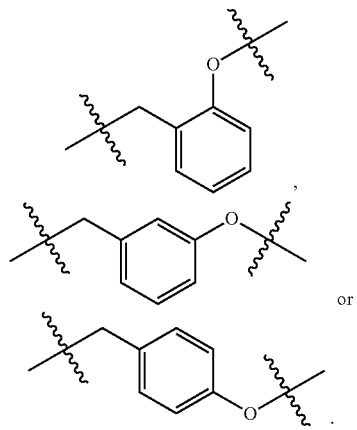

In some embodiments, Y is

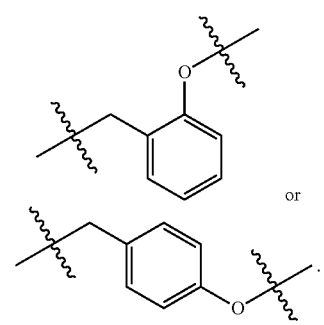

In some embodiments, Y is

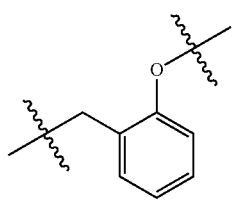

In some embodiments, Y is

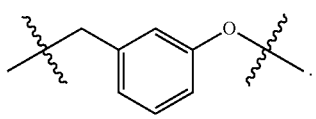 [SMILES: *Cc1cccc(O*)c1]

In some embodiments, Y is

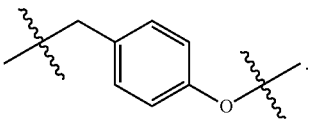 [SMILES: *Cc1ccc(O*)cc1]

In some embodiments, Y is a bond.

In some embodiments, each of m and n is independently an integer having a value of 0, 1, 2, 3, 4, 5, or 6. In some embodiments, each of m and n is independently an integer having a value of 1, 2, 3, 4, 5, or 6. In some embodiments, each of m and n is independently an integer having a value of 2, 3, 4, 5, or 6. In some embodiments, each of m and n is independently an integer having a value of 0, 1, 2, 3, or 4. In some embodiments, each of m and n is independently an integer having a value of 1, 2, 3, or 4. In some embodiments, each of m and n is independently an integer having a value of 0, 1, 2, or 3. In some embodiments, each of m and n is independently an integer having a value of 2, 3, or 4. In some embodiments, each of m and n is independently an integer having a value of 1, 2, or 3. In some embodiments, each of m and n is independently an integer having a value of 2, or 3. In some embodiments, each of m and n is an integer having a value of 1, 2, or 3. In some embodiments, each of m and n is an integer having a value of 2, or 3. In some embodiments, each of m and n is an integer having a value of 2. In some embodiments, each of m and n is an integer having a value of 3.

In some embodiments, o is 1, 2, or 3. In some embodiments, o is 1. In some embodiments, o is 2. In some embodiments, o is 3.

In some embodiments, $R_1$ is 2,3-desoxy-2,3-dehydroglucose, glucoside, mannoside, galactoside, alloside, guloside, idoside, taloside, rhamnoside, maltoside, 2,3-desoxy-2,3-dehydromaltoside, 2,3-desoxymaltoside, lactoside, 2,3-desoxy-2,3-dehydro-lactoside, 2,3-desoxylactoside, glucouronate, glucosamine, galactosamine, mannosamine, N-acetylglucosamine, N-acetylgalactosamine, or N-acetylmannosamine;

$R_2$ is $C_{1-10}$ alkyl or alkene having 1-3 substituents independently selected from the group consisting of halogen atoms, amino, hydroxy, carboxylic acid group, ester, and amide;

$R_3$ is H or loweralkyl;

each $R_4$ and $R_5$ is independently amine, hydroxyl, or carboxylic acid;

$R^x$ is hydroxyl;

each of $R_6$ and $R_7$ is independently a linear or branched, saturated aliphatic $C_2$-$C_{10}$ hydrocarbon chain;

each of $R_8$ and $R_9$ is a linear or branched aliphatic $C_2$-$C_{10}$ hydrocarbon chain, having 1-3 substituents independently selected from the group consisting of halogen atoms, amino, hydroxy, carboxylic acid group, ester, and amide.

$R_{10}$ is —C≡CH, —CH=$CH_2$, or —$CH_2$—$CH_3$;

$R_{11}$ is independently a saturated, unsaturated with at least one double or triple bond, branched or unbranched $C_{1-30}$ alkyl group, optionally substituted with an aliphatic or aromatic $C_{3-9}$ cyclohydrocarbon or heterocyclic group;

Y is a bond or —$CH_2$-aryl-O—, wherein the aryl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —$NH_2$, —$NO_2$, and —CN;

each of m and n is independently an integer having a value of 0, 1, 2, 3, 4, 5, or 6; and o is 1, 2, or 3.

In some embodiments, $R_1$ is 2,3-desoxy-2,3-dehydroglucose, glucoside, mannoside, galactoside, alloside, guloside, idoside, taloside, rhamnoside, maltoside, 2,3-desoxy-2,3-dehydromaltoside, 2,3-desoxymaltoside, lactoside, 2,3-desoxy-2,3-dehydro-lactoside, 2,3-desoxylactoside, glucouronate, glucosamine, galactosamine, mannosamine, N-acetylglucosamine, N-acetylgalactosamine, or N-acetylmannosamine;

$R_2$ is $C_{1-10}$ alkyl or alkene having 1-3 substituents independently selected from the group consisting of halogen atoms, amino, or hydroxyl;

$R_3$ is H or loweralkyl;

each $R_4$ and $R_5$ is independently amine, hydroxyl, or carboxylic acid;

$R^x$ is hydroxyl;

each of $R_6$ and $R_7$ is independently a linear or branched, saturated aliphatic $C_2$-$C_{10}$ hydrocarbon chain;

each of $R_8$ and $R_9$ is a linear or branched aliphatic $C_2$-$C_{10}$ hydrocarbon chain, having 1-3 substituents independently selected from the group consisting of halogen atoms, amino, and hydroxyl;

$R_{10}$ is —C≡CH, —CH═CH$_2$, or —CH$_2$—CH$_3$;

$R_{11}$ is independently a saturated, unsaturated with at least one double or triple bond, branched or unbranched $C_{1-30}$ alkyl group, optionally substituted with an aliphatic or aromatic $C_{3-9}$ cyclohydrocarbon or heterocyclic group; and Y is a bond or —CH$_2$-phenyl-O—, wherein the phenyl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —NH$_2$, —NO$_2$, and —CN.

In some embodiments, $R_1$ is glucoside, mannoside, galactoside, alloside, guloside, idoside, taloside, rhamnoside, maltoside, lactoside, glucouronate, glucosamine, galactosamine, or mannosamine;

$R_2$ is $C_{1-6}$ alkyl;

$R_3$ is H or $C_{1-4}$ alkyl;

each $R_4$ and $R_5$ is independently amine, hydroxyl, or carboxylic acid;

$R^x$ is hydroxyl;

each of $R_6$ and $R_7$ is independently a linear or branched, saturated aliphatic $C_2$-$C_6$ hydrocarbon chain;

each of $R_8$ and $R_9$ is a linear or branched aliphatic $C_2$-$C_6$ hydrocarbon chain;

$R_{10}$ is —C≡CH, —CH═CH$_2$, or —CH$_2$—CH$_3$;

$R_{11}$ is independently a saturated, unsaturated with at least one double or triple bond, branched or unbranched $C_{1-30}$ alkyl group, optionally substituted with an aliphatic or aromatic $C_{3-9}$ cyclohydrocarbon or heterocyclic group; and Y is a bond,

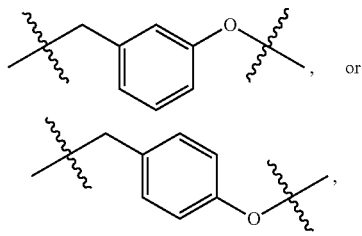, or wherein the phenyl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —NH$_2$, —NO$_2$, and —CN.

In some embodiments, the compound is a compound of formula (I) wherein $R_1$ is a saccharide; $R_2$ is $C_{1-10}$ alkyl or alkene having one carbon substituted by 1-3 of halogen atoms, amino, hydroxy, carboxylic acid group, ester, amide, or cyano wherein one or more of the hydroxy, carboxylic acid or amide group is optionally glycosylated with a saccharide group; $R_3$ is H, halo or loweralkyl; Y is a bond,

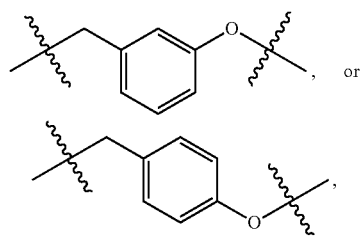, or wherein the phenyl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —NH$_2$, —NO$_2$, and —CN; and n is an integer from 0-6.

In some embodiments of formula (I), $R_1$ is a monosaccharide, disaccharide, or trisaccharide. In some embodiments of formula (I), $R_1$ is a furanose or a pyranose.

In some embodiments of formula (I), $R_1$ is 2,3-desoxy-2,3-dehydroglucose, glucoside, mannoside, galactoside, alloside, guloside, idoside, taloside, rhamnoside, maltoside, 2,3-desoxy-2,3-dehydromaltoside, 2,3-desoxymaltoside, lactoside, 2,3-desoxy-2,3-dehydro-lactoside, 2,3-desoxylactoside, glucouronate, glucosamine, galactosamine, mannosamine, N-acetylglucosamine, N-acetylgalactosamine, or N-acetylmannosamine; $R_2$ is $C_{1-10}$ alkyl or alkene; $R_3$ is H or loweralkyl; and n is an integer from 1-4.

In some embodiments of formula (I), $R_1$ is glucose, mannose, galactose, 2-NAc glucose, or 2-deoxyglucose; $R_2$ is $C_{1-6}$ alkyl; $R_3$ is H; Y is

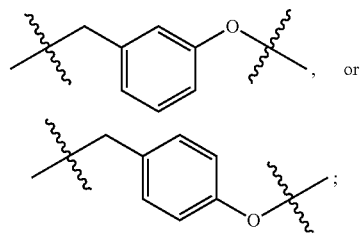, or and n is 2.

In some embodiments of formula (I), $R_1$ is glucose, mannose, galactose, 2-NAc glucose, or 2-deoxyglucose; $R_2$ is $C_{1-6}$ alkyl; $R_3$ is H; Y is a bond; and n is 2.

According to another aspect of the invention, a therapeutically effective amount of a glycosylated valproic acid or analog of the present invention, or a pharmaceutically acceptable salt thereof, is provided in the form of a pharmaceutical composition having at least one pharmaceutically acceptable carrier. Compounds having formula I, II, III, IV, V, or VI may be formulated in a single formulation with another active agent(s), or formulated independently.

According to one aspect of the invention, methods are provided wherein a therapeutically effective amount of a glycosylated valproic acid or analog of the present invention, or a pharmaceutically acceptable salt thereof, is administered to an animal in need thereof.

In some embodiments, the glycosylated valproic acid or analogs comprise a compound of formulas (I)-(VI). In some embodiments, the glycosylated valproic acid or analogs comprise a compound of formula (I). In some embodiments, the glycosylated valproic acid or analogs comprise a compound of formula (II). In some embodiments, the glycosylated valproic acid or analogs comprise a compound of formula (III). In some embodiments, the glycosylated valproic acid or analogs comprise a compound of formula (IV). In some embodiments, the glycosylated valproic acid or analogs comprise a compound of formula (V). In some embodiments, the glycosylated valproic acid or analogs comprise a compound of formula (VI).

In certain embodiments, the saccharide is exemplified by, but not limited to, 2,3-desoxy-2,3-dehydroglucose, glucoside, mannoside, galactoside, alloside, guloside, idoside, taloside, rhamnoside, maltoside, 2,3-desoxy-2,3-dehydromaltoside, 2,3-desoxymaltoside, lactoside, 2,3-desoxy-2,3-dehydro-lactoside, 2,3-desoxylactoside, glucouronate, glucosamine, galactosamine, mannosamine, N-acetylglucosamine, N-acetylgalactosamine, and N-acetylmannosamine. Thus, in certain embodiments, $R_1$ is 2,3-desoxy-2,3-dehydroglucose, glucoside, mannoside, galactoside, alloside, guloside, idoside, taloside, rhamnoside, maltoside, 2,3-desoxy-2,3-dehydromaltoside, 2,3-desoxymaltoside, lactoside, 2,3-desoxy-2,3-dehydro-lactoside, 2,3-desoxylactoside, glucouronate, glucosamine, galactosamine, mannosamine, N-acetylglucosamine, N-acetylgalactosamine, or N-acetylmannosamine In certain embodiments, $R_1$ is 2,3-desoxy-2,3-dehydroglucose, glucoside, mannoside, galactoside, alloside, guloside, idoside, taloside, rhamnoside, maltoside, 2,3-desoxy-2,3-dehydromaltoside, 2,3-desoxymaltoside, lactoside, 2,3-desoxy-2,3-dehydro-lactoside, 2,3-desoxylactoside, or glucouronate.

In certain embodiments, $R_1$ is glucoside, mannoside, galactoside, alloside, guloside, idoside, taloside, rhamnoside, maltoside, lactoside, or glucouronate. In certain embodiments, $R_1$ is glucoside, mannoside, galactoside, alloside, rhamnoside, maltoside, lactoside, or glucouronate. In certain embodiments, $R_1$ is glucoside, mannoside, galactoside, alloside, rhamnoside, maltoside, lactoside. In certain embodiments, $R_1$ is glucoside, mannoside, galactoside or maltoside. In certain embodiments, $R_1$ is glucoside, mannoside or galactoside. In certain embodiments, $R_1$ is glucoside or mannoside. In certain embodiments, $R_1$ is glucoside. In certain embodiments, $R_1$ is mannoside. In certain embodiments, $R_1$ is galactoside.

In some embodiments, the present invention contemplates the use of a saccharide or carbohydrate unit or units having five-membered rings, known as furanoses. In some embodiments, the present invention contemplates the use of carbohydrate unit or units having six-membered rings, known as pyranoses. Combinations of furanoses and pyranoses are also contemplated.

In some embodiments, the saccharide or carbohydrate containing acetate protecting group(s) are exemplified by, but not limited to, 2,3-desoxy-2,3-dehydroglucose diacetate, glucoside tetraacetate, mannoside tetraacetate, galactoside tetraacetate, alloside tetraacetate, guloside tetraacetate, idoside tetraacetate, taloside tetraacetate, rhamnoside triacetate, maltoside heptaacetate, 2,3-desoxy-2,3-dehydromaltoside pentaacetate, 2,3-desoxymaltoside pentaacetate, lactoside tetraacetate, 2,3-desoxy-2,3-dehydrolactoside pentaacetate, 2,3-desoxylactoside pentaacetate, glucouronate triacetate, N-acetylglucosamine triacetate N-acetylgalactosamine tiacetate, and N-acetylmannosamine triacetate. In some embodiments, the present invention contemplates the use of carbohydrate unit or units having five-membered rings, known as furanoses. In some embodiments, the present invention contemplates the use of carbohydrate unit or units having six-membered rings, known as pyranoses. Combinations of furanoses and pyranoses are also contemplated.

In some embodiments, the saccharide or carbohydrate attached to the drug contain protecting groups exemplified by, but not limited to, an acetyl group, including acetyl (Ac), chloroacetyl (ClAc), propionyl, benzoyl (Bz), and pivaloyl (Piv). Non-acyl protecting groups include, but are not limited to, benzyl (Bn), β-methoxyethoxymethyl ether (MEM), methoxymethyl ether (MOM), p-methoxybenzyl ether (PMB), methylthiomethyl ether, tetrahydropyran (THP), silyl ethers (including, but not limited to, trimethylsilyl (TMS), tert-butyldimethylsilyl (TBDMS), and triisopropylsilyl (TIPS) ethers), methyl ethers, and ethoxyethyl ethers (EE). In some embodiments, the saccharide or carbohydrate attached contains a protecting group exemplified by, but not limited to, amine protecting groups such as a carbobenzyloxy (Cbz) group, p-methoxybenzyl carbonyl (Moz or MeOZ) group, tert-butyloxycarbonyl (BOC) group, 9-fluorenylmethyloxycarbonyl (FMOC) group, benzyl (Bn) group, p-methoxybenzyl (PMB), dimethoxybenzyl (DMPM), p-methoxyphenyl (PMP) group, tosyl (Ts) group, and other sulfonamide (Nosyl & Nps) groups. In some embodiments, the saccharide or carbohydrate attached contains a protecting group exemplified by, but not limited to, carbonyl protecting groups such as acetals, ketals, acylals, and dithianes. Exemplary carboxylic acid protecting groups include, without limitation, alkyl esters, aryl esters, and silyl esters.

In some embodiments, glycosylated valproic acids or analogs of the present invention reduce the incidence of resistance from developing. Without being bound by theory, by attaching a sugar to the compound (e.g., valproic acid or analog), the sugar not only allows greater uptake of the compound into the cell, but also prevents it from being ejected from the cell and thus improves efficacy. For example, putting a sugar on the compound reduces the p-glycoprotein pumping effect to cause the compound to be ejected. Thus, without being bound by theory, it is believed that putting a sugar on valproic acid improves the compounds efficacy over time. In some embodiments, the compound of any of formulas I-VI comprises a sugar to reduce drug resistance.

In one aspect, the invention provides methods of treating, ameliorating, or preventing viral infections comprising administering to an animal in need thereof a therapeutically effective amount of a compound of any of formulas I-VI. In some embodiments, the viral infection is an HIV infection.

In one aspect, the invention provides methods of treating or ameliorating cancer comprising administering to an animal in need thereof a therapeutically effective amount of a compound of any of formulas I-VI.

In some embodiments, cancer is selected from the group consisting of colon cancer, brain cancer, glioma, multiple myeloma, head and neck cancer, hepatocellular cancer, melanoma, ovarian cancer, cervical cancer, renal cancer, and non-small cell lung cancer. In a further embodiment, the cancer is acute and chronic lymphocytic leukemia, acute granulocytic leukemia, adrenal cortex carcinoma, bladder carcinoma, breast carcinoma, cervical carcinoma, cervical hyperplasia, choriocarcinoma, chronic granulocytic leukemia, chronic lymphocytic leukemia, colon carcinoma, endometrial carcinoma, esophageal carcinoma, essential thrombocytosis, genitourinary carcinoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, osteogenic sarcoma, ovarian carcinoma, pancreatic carcinoma, polycythemia vera, primary brain carcinoma, primary macroglobulinemia, prostatic carcinoma, renal cell carcinoma, rhabdomyosarcoma, skin cancer, small-cell lung carcinoma, soft-tissue sarcoma, squamous cell carcinoma, stomach carcinoma, testicular carcinoma, thyroid carcinoma, or Wilms' tumor of the kidney.

In another aspect, the invention provides methods of inhibiting neuroinflammation associated with traumatic brain injury comprising administering to an animal in need thereof a therapeutically effective amount of a compound of any of formulas I-VI.

In another aspect, the invention provides methods of inhibiting histone deacetylase I (HDAC-1) and histone deacetylases II (HDAC-2s) comprising administering to an animal in need thereof a therapeutically effective amount of a compound of any of formulas I-VI.

In another aspect, the invention provides methods of treating a disease or a condition associated with degeneration of muscle tissue, comprising identifying a subject suffering from a disease or condition associated with degeneration of muscle tissue, nerve tissue, or hematopoietic tissue and administering to the subject a therapeutically effective amount of a compound of any of formulas I-VI. In some embodiments, the glycosylated valproic acid or analog is administered with an HDAC inhibitor.

In another aspect, the invention provides methods of treating a central nervous system (CNS) in a subject in need of treatment comprising administering to said subject a therapeutically effective amount of a compound of any of formulas I-VI. In some embodiments, the subject has Alzheimer's disease, Senile dementia, Huntington's disease, torsion dystonia, spasmodic torticollis, Gilles de la Tourette syndrome, and/or Parkinson's disease In another aspect, the invention provides methods of treating a cancer in a subject in need of such treatment, the method comprising administering to the subject a therapeutically effective amount of a compound of any of formulas I-VI to induce apoptosis in the cancer. In some embodiments, the cancer is associated with the P53 gene. In some embodiments, the compound of any of formulas I-VI is used in combination with a chemotherapeutic agent to enhance sensitivity of the cancer to radiotherapy. In some embodiments, the compound of any of formulas I-VI is used in conjunction with SBHA as a Notch 1 activator to suppress NE tumor markers and reduce growth of cancer via apoptosis of pheochromocytoma cells. In some embodiments, the compound of any of formulas I-VI is used to induce apoptosis of undifferentiated cancer cells.

In another aspect, the invention provides methods of treating an asthmatic condition or COPD in a subject in need of such treatment, the method comprising administering to the subject a therapeutically effective amount of the compound of any of formulas I-VI to regulate the expression of distinct subsets of inflammatory/immune genes to enhance an activity of antigen-induced contraction of lung membranes.

In another aspect, the invention provides methods of screening an array of cDNA, the method comprising contacting the cDNA with the compound of any of formulas I-VI. In some embodiments, the compound of any of formulas I-VI can target genes regulated by valproic acid to reprogram stem cells and/or undifferentiated progenitor cells.

In another aspect, the invention provides methods of treating a disease or condition in a subject in need of such treatment, the method comprising administering to the subject a therapeutically effective amount of the compound of any of formulas I-VI to treat the disease or condition associated with degeneration of muscle tissue, nerve tissue, or hematopoietic tissue, wherein the disease or condition is muscular atrophy, muscular dystrophy, muscular cachexia, dermatomyositis, Alzheimer's disease, olivopontocerebellar atrophy, Parkinson's disease, degeneration of nervous tissue, occular atrophy, alcohol-induced brain damage, hepatocerebral degeneration, idiopathic aplastic anemia, secondary aplastic anemia, post-ischemic tissue degeneration, amyotrophic lateral sclerosis, poliomyelitis, polyglutamine expansion diseases, bone marrow loss induced by radiation therapy or chemotherapy, multiple myeloma, acute lymphocytic leukemia, HIV infection, AIDS, malaria, chronic myelogenous leukemia, Senile dementia, Huntingtons disease, Parkinsons disease, epilespsy, torsion dystonia, Tourettes Fanconi's anemia, trauma or a combination thereof. In some embodiments, the compound of any of formulas I-VI is administered alone or in combination with other therapeutic agents for the disease or condition. In some embodiments, the compound of any of formulas I-VI is an inhibitor of tyrosine and/or serine/threonine kinases and tyrosine kinase receptors involved in cellular signaling. In some embodiments, the other therapeutic agent includes at least one of a natural product, an antimetabolite, an alkylating agent, a plant derived product including an alkaloid, a chemotherapeutic agent, an anti-angiogenic agent, a Hsp90 inhibitor, an HDAC inhibitor or a combination thereof.

In another aspect, the invention provides methods of producing a totipotent tissue culture, the method comprising providing a tissue culture and growing the tissue culture on a medium which contains an effective amount of a compound of any of formulas I-VI produce the totipotent tissue culture.

In some embodiments, the compound of any of formulas I-VI can be used in (i) reprogramming of adult cells to a totipotent state; (ii) reprogramming of adult cells; (iii) increasing a rate of cell proliferation; and/or (iv) in organ regeneration.

In some embodiments, the compound of any of formulas I-VI is used in combination with gene therapy.

The term "alkyl" as used herein refers to an unsaturated acyclic hydrocarbon radical. The term "lower alkyl" refers to acyclic hydrocarbon radicals containing from about 2 to about 10 carbon atoms, preferably from about 2 to about 8 carbon atoms and more preferably 1 to about 6 carbon atoms. Examples of suitable alkyl radicals include methyl, ethyl, propyl, butyl, isobutyl, pentyl, 2-methylbutyl, 3-methylbutyl, hexyl, heptyl, and octyl, and the like.

The term "alkenyl" as used herein refers to a straight or branched chain radical of 2-10 carbon atoms including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein refers to a straight or branched chain radical of 2-10 carbon atoms wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

The term "carbocycle" as used herein include cyclic hydrocarbons that are saturated (e.g., cycloalkyl), partially unsaturated (e.g., cycloalkenyl) or fully unsaturated (e.g., aryl groups including phenyl). Useful cycloalkyl groups are, for example, $C_{3-8}$ cycloalkyl. Typical cycloalkyl groups include cyclopropyl, cyclobutyl, cyclopentyl, cyclohexyl and cycloheptyl. Useful partially saturated carbocyclic groups include, for example, cycloalkenyl groups, such as cyclopentenyl, cycloheptenyl and cyclooctenyl.

The term "aryl" as employed herein by itself or as part of another group refers to monocyclic, bicyclic or tricyclic aromatic groups containing from 6 to 14 carbons in the ring portion. Useful aryl groups include, for example, $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful halo or halogen groups include fluorine, chlorine, bromine and iodine.

The term "prodrug" as used herein refers to variations or derivatives of the compounds of this invention which have groups cleavable under metabolic conditions to form the compounds of the present invention. Thus, prodrugs of the present invention become the compounds of the invention when they undergo solvolysis under physiological conditions or undergo enzymatic degradation (e.g., hydrolysis), or oxidation (e.g., hepatic hydroxylation) or reduction. The prodrug itself may or may not also have HDAC inhibitory activity.

Typical enzymatically or solvolytically cleavable groups suitable for preparing the prodrugs of the present invention include esters, imines, carbamates, acetals and ketals. For example, an ester of a carboxylic acid containing compound of the present invention may be prepared by condensation with an alcohol, preferably a lower alkyl alcohol, more preferably a $C_{1-4}$ alkyl alcohol. Similarly, an ester of a hydroxy containing compound of the present invention may be prepared by condensation with a carboxylic or a dioic acid, preferably an alkyl carboxylic or dioic acid, more preferably a $C_{1-4}$ carboxylic acid or a $C_{3-6}$ dioic acid or anhydride thereof. Moreover, an imine of an amino containing compound of the present invention may be obtained by condensation of the amino group with a carbonyl group of an aldehyde or a ketone. Aldehydes and ketones suitable for condensation with amino containing compounds of the present invention include alkyl and aryl ketones and aldehydes, more preferably alky ketones and aldehydes, more preferably lower alkyl ketones and aldehydes, most preferably $C_{1-4}$ alkyl aldehydes and ketones. A carbamate of an amino containing compound of the present invention may be prepared by condensation of the amino group with, for example, benzyloxycarbonyl chloride. In addition, an acetal or ketal of an alcohol containing compound of the present invention may be obtained by condensation of the hydroxy group with chloromethyl methyl ether or chloromethyl ethyl ether.

In some embodiments, glycosylated valproic acid and/or its analogs include its structurally and functionally related forms. In some embodiments, this includes a sugar attached to either valproic acid or a compound similar to valproic acid. In some embodiments, glycosylated valproic acid analogs, include but are not limited to, glycosylated carboxylic acid analogs.

Glycosylated valproic acid and analogs of the present invention can be provided as pharmaceutically acceptable salts. Examples of pharmaceutically acceptable salts (i.e., addition salts) include inorganic and organic acid addition salts such as hydrochloride, hydrobromide, phosphate, sulphate, citrate, lactate, tartrate, maleate, fumarate, mandelate, benzoate and oxalate; and inorganic and organic base addition salts with bases such as sodium hydroxide, Tris(hydroxymethyl)aminomethane (TRIS, tromethane), ammonium hydroxide, and tetra-substituted-ammonium hydroxide (e.g, tetramethlammonium hydroxide). Although the salts typically have similar physiological properties compared to the free base, certain acid addition salts may demonstrate preferred physicochemical properties, e.g., enhanced solubility, improved stability. One particular pharmaceutically acceptable salt is derived from maleic acid, the salt being either a hydrogen maleate or a dimaleate salt.

Salts may also be derived from inorganic bases such as aluminum, calcium, copper, ferric, ferrous, lithium, magnesium, manganic salts, manganese, potassium, sodium, zinc and the like.

According to one aspect of the invention, methods for treating, ameliorating, or preventing viral infections, wherein a therapeutically effective amount of a glycosylated valproic acid or analog of the present invention, or a pharmaceutically acceptable salt thereof, is administered to an animal in need thereof. In certain embodiments of the invention, the viral infection is latent HIV infection.

According to some embodiments of the invention, the glycosylated valproic acid or its analog can be combined with an integrase inhibitors (e.g., isentress, raltegravir, elvitegravir, dolutegravir or the like). Without being bound by theory, the use of valproic acid and an integrase inhibitor to reduce latent HIV infections may occur by opening up the chromatin package to the various HIV cocktails. It is intended to use a glycosylated form of valproic acid to improve the treatment mode of reducing latent HIV.

In some embodiments, glycosylated valproic acid and analogs of the present invention are potent inhibitors of Class I histone deacetylases (Class I HDACs), including histone deacetylase 1 (HDAC-1), histone deacetylase 2 (HDAC-2), histone deacetylase 3 (HDAC-3) and/or histone deacetylase 8 (HDAC-8). In particular embodiments, glycosylated valproic acid and analogs of the present invention are potent inhibitors of histone deacetylase 1 (HDAC-1). In other embodiments, glycosylated valproic acid and analogs of the present invention are potent inhibitors of Class II histone deacetylases (Class II HDACs), including histone deacetylase 4 (HDAC-4), histone deacetylase 5 (HDAC-5), histone deacetylase 6 (HDAC-6), histone deacetylase 7 (HDAC-7) and/or histone deacetylase 9 (HDAC-9).

It has been reported that HDAC inhibitors activate the p53 molecule through acetylation of 320 and 373 lysine residues, upregulate PIG3 and NOXA and induce apoptosis in cancer cells expressing wild and pseudo-wild type p53 genes (Terui T, et al. *Cancer Res* 2003; 63:8948-54; herein incorporated by reference in its entirety). Thus, one aspect of the present invention is the use of glycosylated valproic acid and analogs of the present invention, or a pharmaceutically acceptable salt thereof, to induce apoptosis in cancer cells.

It has been reported (see, for example, U.S. Pat. No. 5,672, 746; herein incorporated by reference in its entirety) that the structure activity relationships of teratogenic valproate-related compounds suggest a strict structural requirement for high teratogenic potency. Molecules that are highly teratogenic were reported to require an α-hydrogen atom, a free carboxyl function, and branching on carbon atom 2 with two chains containing three carbons each for maximum teratogenic activity. Substances that do not conform with these strict structural requirements are of very low or negligible teratogenic activity, but still often exhibit good anticonvulsant activity in several experimental models. Thus, some embodiments of the present invention are valproic acid analogs having a substituent at α carbon.

It has been reported that valproic acid induces apoptosis, modulates differentiation gene expression of thyroid tumors and enhances the sensitivity of anaplastic cancer cell lines to doxorubicin (Kim et al, *Int. J. Oncol.*, 2009, 34(5), 1353-62; herein incorporated by reference in its entirety). Thus, some embodiments of the present invention include use of a glycosylated valproic acid or analog of the present invention, or a pharmaceutically acceptable salt thereof, to treat thyroid cancers.

It has been reported that HDAC inhibitors can enhance both the in vitro and in vivo radiosensitivity of human tumor cell lines generated from a spectrum of solid tumors (Camphausen et al, *Int. J. Cancer*, 2005, 114(3), 380-386; Chinnaiyan et al, *Clin. Cancer Res.* 2008, 14, 5410; each herein incorporated by reference in its entirety). Additional studies have used HDAC inhibitors in clinical trials as single modalities, in combination with chemotherapeutic agents, and recently, in combination with radiotherapy. Thus, one aspect of the present invention is to use glycosylated valproic acid and analogs of the present invention, or a pharmaceutically acceptable salt thereof, in combination with radiotherapy.

It has been reported that histone deacetylase (HDAC) inhibitor, 4-dimethylamino-N-[5-(2-mercaptoacetylamino) pentyl]benzamide (DMA-PB), inhibits neuroinflamation associated with traumatic brain injury (Dash et al., "Valproate Administered after Traumatic Brain Injury Provides Neuroprotection and Improves Cognitive Function in Rats," PLoS ONE 2010, 5(6): e11383; Shein et al., *Mol. Med.* 2011, 17(5-6), 448-456; Peterson et al., *Methods in Cell Biol.* 2004, 76, 569-591; each herein incorporated by reference in its entirety). Thus, one aspect of the present invention is to use glycosylated valproic acid and analogs of the present invention, or a pharmaceutically acceptable salt thereof, to treat traumatic brain injuries.

HDACs act to regulate the expression of distinct subsets of inflammatory/immune genes. HDAC2 expression and activity is reduced in lung macrophages, biopsy specimens, and blood cells from patients with severe asthma and smoking-induced asthma, as well as in patients with chronic obstructive pulmonary disease, perhaps accounting for the enhanced inflammation and reduced steroid responsiveness seen in these patients. It has recently been reported that certain HDAC inhibitors inhibit antigen-induced contraction of sensitised guinea pig tracheal rings as well as contraction induced by histamine, 5-hydroxytryptamine and carbachol (G-protein coupled receptor agonists), while sodium butyrate (1 mM) and sodium valproate (100 microM) were weak inhibitors. Bhaysar P. et al. *J. Allegy Clin. Immunol.* 121: 580-4 (2008); herein incorporated by reference in its entirety. Thus, one object of the present invention is to enhance the bioavailability, and thus the activity, of valproic acid derivatives.

Valproic acid and suberoyl bis-hydroxamic acid (SBHA) have been demonstrated recently to be strong Notch-1 activators. Upregulation of the Notch-1 pathway has been shown to limit growth and suppress hormonal secretion in neuroendocrine (NE) neoplasms. HDAC inhibitor treatment caused a dose-dependent decrease in ASCL1 and CgA while increasing the amount of active Notch-1 protein; with a 6-day treatment, dose-dependent growth inhibition and cleavage of the apoptotic markers caspase-3 and poly-ADP ribose phosphate was observed. Adler J. T. et al. *Surgery*, 144:956-61 (2008); herein incorporated by reference in its entirety. Thus, one aspect of the invention is to use glycosylated valproic acid and analogs of the present invention, or pharmaceutically acceptable salts thereof, to upregulate Notch-1 effectively, suppress NE tumor markers, and decrease growth via apoptosis of pheochromocytoma cells in vitro.

Certain embodiments of the present invention may be suitable to induce apoptosis of undifferentiated cancer cells. As such, some embodiments of the present invention induce apoptosis in, for example, carcinoma cells, breast cancer cells, colon carcinoma cells and leukemia cells. Whether the compound of the present invention induce apoptosis in a cancer cell line may be assessed by observing morphological alterations and specific marker gene or protein expression.

Another aspect of the present invention relates to methods for treating, ameliorating, or preventing neoplasm and other proliferative disorders. In certain embodiments, the disorder is cancer. In some embodiments, the cancer is selected from the group consisting of colon cancer, brain cancer, glioma, multiple myeloma, head and neck cancer, hepatocellular cancer, melanoma, ovarian cancer, cervical cancer, renal cancer, and non-small cell lung cancer. In a further embodiment, the cancer is acute and chronic lymphocytic leukemia, acute granulocytic leukemia, adrenal cortex carcinoma, bladder carcinoma, breast carcinoma, cervical carcinoma, cervical hyperplasia, choriocarcinoma, chronic granulocytic leukemia, chronic lymphocytic leukemia, acute myeloid leukemia, chronic myelogenous leukemia, colon carcinoma, endometrial carcinoma, esophageal carcinoma, essential thrombocytosis, genitourinary carcinoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, osteogenic sarcoma, ovarian carcinoma, pancreatic carcinoma, polycythemia vera, primary brain carcinoma, primary macroglobulinemia, prostatic carcinoma, renal cell carcinoma, rhabdomyosarcoma, skin cancer, small-cell lung carcinoma, soft-tissue sarcoma, squamous cell carcinoma, stomach carcinoma, testicular carcinoma, thyroid carcinoma, and Wilms' tumor.

A further aspect of the invention is the use of a glycosylated valproic acid or analog of the present invention for the manufacture of a medicament for the treatment of a disease in which the inhibition of HDAC has a beneficial effect. In some embodiments, the beneficial effect results in apoptosis of a patient's tumor cells, thus causing a clinical improvement of the patient's condition. Examples of such diseases are skin cancer, estrogen receptor-dependent and independent breast cancer, ovarian cancer, prostate cancer, renal cancer, colon and colorectal cancer, pancreatic cancer, head and neck cancer, small cell and non-small cell lung carcinoma. Inhibition of HDAC may also be beneficial by reverting inappropriate gene expression in diseases based on aberrant recruitment of histone deacetylase activity such as thyroid resistance syndrome.

Another aspect of the invention is the use of a glycosylated valproic acid or analog of the present invention to define genes induced by the compounds in cells such as primary animal cells as well as cancer cell lines. Methods to define genes induced by glycosylated valproic acid and analogs of the present invention include established technologies for screening large arrays of cDNAs, expressed sequence tags or so-called unigene collections (EP Patent 1,170,008; herein incorporated by reference in its entirety). Also the use of subtractive hybridization techniques is suitable to define genes which are induced by glycosylated valproic acid and analogs of the present invention. Identification of potential targets for HDAC-inhibition facilitates the therapeutic treatment of patients with a glycosylated valproic acid or analog of the present invention. Considering the low general toxicity of valproic acid in the organism compared to other HDAC-inhibitors, glycosylated valproic acid and analogs of the present invention are suitable for targeting genes regulated by valproic acid.

HDAC inhibitors promote differentiation, growth, and regeneration of undifferentiated progenitor cells, if the undifferentiated progenitor cells are contacted with an HDAC inhibitor during a stage of development, such as during the myoblast stage. While protein acetylation promotes muscle transcription and differentiation, HDAC inhibitors can repress muscle-gene transcription and cellular differentiation in differentiated myotubes. Thus, another aspect of the invention is a method of treating a disease or a condition associated with degeneration of muscle tissue, comprising identifying a subject suffering from a disease or condition associated with degeneration of muscle tissue and administering to the subject a therapeutically effective amount of glycosylated valproic acid or analog of the present invention, thereby treating the disease or condition associated with degeneration of muscle tissue. In some embodiments, HDAC inhibitor is part of a method of treating a disease or condition associated with degeneration of muscle tissue, nerve tissue, or hematopoietic tissue. In some embodiments, the conditions associated with the tissue degeneration may be those that destroy tissue, reduce cellular size or number within a tissue, impair the functioning of tissue, or otherwise diminish a mass of tissue, for example, through non-use (such as muscular atrophy), an infective agent (such as viral destruction of cells), a toxin (such as bone marrow loss during chemotherapy), or genetic mutation (such as anemia). In a some embodiments, the conditions associated with the tissue degeneration include muscular atrophy, muscular dystrophy, muscular cachexia, dermatomyositis, Alzheimer's disease, olivopontocerebellar atrophy, Parkinson's disease, degeneration of nervous tissue, occular atrophy, alcohol-induced brain damage, hepatocerebral degeneration, idiopathic aplastic anemia, secondary aplastic anemia, post-ischemic tissue degeneration, amyotrophic lateral sclerosis, poliomyelitis, bone marrow loss induced by radiation therapy or chemotherapy, multiple myeloma, acute lymphocytic leukemia, HIV infection, AIDS, malaria, chronic myelogenous leukemia, Fanconi's anemia, and/or trauma Additionally, administering an HDAC inhibitor such as glycosylated valproic acid or analog of the present invention to a subject may provide a prophylactic effect leading to the inhibition or prevention of such diseases or conditions. Thus, a subject at risk of suffering some muscle-wasting disease, such as muscular dystrophy, and/or some neurodegenerative disease, such as Alzhiemer's disease, may be administered an amount of an amount of an HDAC inhibitor such as glycosylated valproic acid or analog of the present invention effective to promote growth and differentiation of progenitor cells within that subject, thus replacing dead or dying cells of muscle or nervous tissue. Thus, another aspect of the invention is a method of preventing conditions associated with tissue degeneration by administering to a subject at risk of the condition an amount of glycosylated valproic acid or analog of the present invention sufficient to prevent the condition.

In another aspect, the present invention relates to a method of treating a disease of the central nervous system (CNS) in a subject in need of treatment comprising administering to said subject a therapeutically effective amount of glycosylated valproic acid and analogs described herein.

In another aspect, the present invention relates to the use of any one or more of glycosylated valproic acid and analogs disclosed herein in the preparation of a medicament for the treatment of a disease of the central nervous system (CNS) in a subject in need of such treatment.

In some embodiments, the CNS disease is a neurodegenerative disease including those inherited neurodegenerative diseases that are polyglutamine expansion diseases. In some embodiments, the neurodegenerative disease is a disorder characterized by progressive dementia in the absence of other prominent neurologic signs, such as Alzheimer's disease; senile dementia of the Alzheimer type; and Pick's disease (lobar atrophy). In some embodiments, the neurodegenerative disease is a syndrome combining progressive dementia with other prominent neurologic abnormalities such as Huntington's disease, multiple system atrophy combining dementia with ataxia and/or manifestations of Parkinson's disease, progressive supranuclear palsy (Steel-Richardson-Olszewski), diffuse Lewy body disease, or corticodentatonigral degeneration. In some embodiments, the syndromes appear mainly in children or young adults (e.g., Hallervorden-Spatz disease and progressive familial myoclonic epilepsy) or are those gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

One further aspect of the invention relates to methods for producing totipotent tissue culture comprising selecting living tissue and cultivating the tissue on a medium which contains an effective amount of a glycosylated valproic acid or analog of the present invention, or a pharmaceutically acceptable salt thereof, to produce totipotent tissue. The totipotent tissue may be transferred to a second medium for cultivating and growing the tissues. In some embodiments, the living tissues may be harvested from a subject in need of treatment with totipotent tissues or from a donor.

Glycosylated valproic acid and analogs of the present invention can be administered alone or in combination with other therapies suitable for the disease or disorder being treated. Where separate dosage formulations are used, the valproic acid derivative and the other therapeutic agent can be administered concurrently or sequentially. The pharmaceutical combination is understood to include all these regimens. Administration in these various ways is suitable for the present invention as long as the beneficial therapeutic effect of the valproic acid derivative and the other therapeutic agent are realized at the desired time.

Glycosylated valproic acid and analogs of the present invention can be used in conjunction with stem cells. Stem cells have the potential for unlimited rounds of replication and are capable of generating all the mature specialized cell types through differentiation found in the adult such as skin cells, bone marrow, bone, liver and cartilage.

Stem cells can also be pluripotent which are stem cells able to differentiate into any of three germ cell layers (1) mesoderm which form lungs, the GI tract and the lining of the stomach, (2) ectoderm which form bones, muscles, blood and the urogenital tract, and (3) the ectoderm which forms skin and the nervous system.

It has been determined that mature specialized cells are not necessarily immortally committed. Initially, viruses and four expressed genes were able to reprogram or induce pluripotency in adult cells. Since then, valproic acid (an HDAC inhibitor) has been shown to be able to eliminate the use of potentially dangerous viruses and two of the four genes in stem cell reprogramming. Hunter, A. L. and Cooke, J. P. Nonviral Reprogramming: Toward a Safer Induced Pluripotent Stem Cell, in Advances in Wound Care, vol. 2, Ch. 4 (2011); Huangfu et al. *Nat. Biotechnol.* 2008, 26(7), 795-7; each herein incorporated by reference. Additionally, valproic acid demonstrates much greater potency. Thus, in some embodiments, the glycosylated valproic acid and analogs can be used in stem cell reprogramming.

Histone deacetylases (HDACs) are enzymes which tighten the chromatin package which inhibits transcription. Histone deacetylase inhibitors counter the HDACs, allowing the chromatin package to unwind and allowing transcription. Weinhold, B. 2006. Epigenetics: The Science of Change. *Environ Health Perspect* 114:A160-A167; Hunter, A. L. and Cooke, J. P. "Nonviral Reprogramming: Toward a Safer Induced Pluripotent Stem Cell," in Advances in Wound Care, vol. 2, Ch. 4 (2011); each herein incorporated by reference in its entirety. Thus, HDAC inhibitors such as valproic acid play a major role in the field of stem cell proliferation and, as a result, in the field of tissue and organ regeneration. Thus, the glycosylated valproic acid and analogs can be used in the field of tissue and organ regeneration.

In another aspect, the glycosylated valproic acid and analogs can be used in both reprogramming of adult cells to the totipotent state and further on to other adult cells, and in stem cell proliferation in the rate of growth of those cells. Thus glycosylated valproic acid and analogs can be used as a tool in organ regeneration, and as a tool kit in that field for improving the rate of cell proliferation.

In addition, in the CNS and in the muscle wasting field, glycosylated valproic acid and analogs can be used in gene therapy. For example, there may be benefits in cardiac muscle regeneration. Thus, the use of glycosylated valproic acid and analogs extends to cardiac hypertrophy.

Glycosylated valproic acid and analogs of the present invention may be administered in combination with one or more active agents. Examples of active agents suitable for combination with valproic acid derivatives of the present invention include HDAC inhibitors, alkylating agents, antibiotic agents, antimetabolic agents, hormonal agents, plant-derived agents, anti-angiogenic agents, differentiation inducing agents (such as those described in U.S. Pat. Nos. RE40,703; 7,279,331; RE39,754; 6,794,392; 6,281,214; and 5,278,155; each herein incorporated by reference in its entirety) retinoid receptor modulators, cytotoxic/cytostatic agents, chemotherapeutic agents, HMG-CoA reductase inhibitors, prenyl-protein transferase inhibitors (such as those described in U.S. Pat. Nos. 6,610,722; 6,562,823; 6,387,903; 6,358,956; and 6,316,436; and in International Patent Application publications WO/2001/051125, WO2001/007046, WO/2000/051614, WO/1999/010329, EP1158984, and EP1324985; each herein incorporated by reference in its entirety), any agent that interferes with cell cycle checkpoints, inhibitors of cell proliferation and survival signaling, apoptosis inducing agents, cell growth arrest inducing agents, or any combination thereof. In addition, the compounds of the present invention are particularly useful when co-administered with radiation therapy.

In some embodiments, glycosylated valproic acid and analogs of the present invention may be administered in combination with an inhibitor of tyrosine and/or serine/threonine kinases and tyrosine kinase receptors involved in cellular signaling. Examples of kinase receptors involved in cellular signaling include Src, AbI, Platelet Derived Growth Factor Receptors, Vascular Endothelial Growth Factor Receptors, c-Met, Fibroblast Growth Factor receptors, Epidermal Growth Factor Receptors, Insulin Growth Factor Receptors, mTOR, Flt-3, CSF-I Receptor, AKT, Polo kinases, Aurora Kinases, STAT-3, PI-3 Kinase, Ras, Raf and Mitogen Activated Kinases, MEK, and ERK. Examples of tyrosine kinase and serine/threonine kinase inhibitors include AMG706, ZA6474, BAY 43-9006, Sunitinib, Dasatinib, CEP-701, XL647, XL999, Lapatinb, Imatinib, MLN518/CT53518, PKC412, ST1571, AMN107, AEE 788, OSI-930, OSI-817, SU1 1248, AG-03736, GW-786034m, and CEP-7055.

HMG-CoA reductase inhibitors that may be combined with glycosylated valproic acid and analogs of the present invention include atorvastatin (LIPITOR®), fluvastatin (LESCOL®), lovastatin (MEVACOR®), pravastatin (PRAVACHOL®), simvastatin (ZOCOR®) and rosuvastatin (CRESTOR®).

HDAC inhibitors that may be combined with glycosylated valproic acid or analog of the present invention include derivatives of valproic acid known to those skilled in the art, hydroxamic acid derivatives, cyclic tetrapeptides, benzamides, and electrophilic ketones. The hydroxamic acid derivatives that may be combined with glycosylated valproic acid and analogs of the present invention may be suberoylanilide hydroxamic acid (SAHA), m-carboxycinnamic acid bishydroxamide (CBHA), pyroxamide, trichostatin analogues such as trichostatin A (TSA) and trichostatin C, salicylhydroxamic acid, suberoyl bishydroxamic acid (SBHA), azelaic bishydroxamic acid (ABHA), azelaic-1-hydroxamate-9-anilide (AAHA), 6-(3-chlorophenylureido) carpoic hydroxamic acid (3Cl-UCHA), oxamflatin [(2E)-5-[3-[(phenylsulfonyl)aminol phenyl]-pent-2-en-4-ynohydroxamic acid], scriptaid, PXD-101 (Prolifix), LAQ-824, CHAP, MW2796, MW2996 or any of the hydroxamic acids disclosed in U.S. Pat. Nos. 5,369,108; 5,932,616; 5,700,811; 6,087,367; and 6,511,990; each herein incorporated by reference in its entirety. The cyclic tetrapeptides that may be combined with glycosylated valproic acid and analogs of the present invention include trapoxin A (TPX)-cyclic tetrapeptide (cyclo-(L-phenylalanyl-L-phenylalanyl-D-pipecolinyl-L-2-amino-8-oxo-9,10-epoxy decanoyl)), FR901228 (FK 228, depsipeptide), FR225497 cyclic tetrapeptide, apicidin cyclic tetrapeptide[cyclo(N—O-methyl-L-tryptophanyl-L-isoleucinyl-D-pipecolinyl-L-2-amino-8-oxodecanoyl)], apicidins (Ia, Ib, Ic, IIa, and IIb), HC-toxin cyclic tetrapeptide, WF27082 cyclic tetrapeptide, or chlamydocin. Other HDAC Inhibitors that may be combined with glycosylated valproic acid and analogs of the present invention include natural products, psammaplins and Depudecin.

Alkylating agents that may be combined with glycosylated valproic acid and analogs of the present invention include bischloroethylamines or nitrogen mustards (such as chlorambucil, cyclophosphamide, ifosfamide, mechlorethamine, melphalan, or uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin, oxaliplatin, and cisplatin), and fluorouracil (5-FU) and other pyrimidine analogs.

Antimetabolic agents or antimetabolites that may be combined with glycosylated valproic acid and analogs of the present invention include enocitabine, carmofur, tegafur, pentostatin, doxifluridine, trimetrexate, fludarabine, capecitabine, galocitabine, cytarabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl] adenine, aplidine, ecteinascidin, troxacitabine, 4-[2-amino-4-oxo-4,6,7,8-tetrahydro-3H-pyrimidino[5,4-b][1,4]thiazin- 6-yl-1-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetr-acyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone, trastuzumab, 5-fluorouracil, methotrexate, cytosine arabinoside, hydroxyurea, gemcitabine, paclitaxel, 6-mercaptopurine, 6-thioguanine, and dacarbazine.

Plant-derived agents that may be combined with glycosylated valproic acid and analogs of the present invention include alkaloids and analogues such as vincristine, vinbalstine, vindesine, vinorelbine.

Chemotherapeutic agents that may be combined with glycosylated valproic acid and analogs of the present invention include abarelix, actinomycin D, aldesleukin, alemtuzumab, alitretinoin, ailopurinol, altretamine, amifostine, anastrozole, arsenic trioxide, asparaginase, azacitidine (5-azacytidine, SAzaC), azathioprine, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, SN-38, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, and zoledronate. In some embodiments, the chemotherapeutic agent is a cocktail such as FEC-100 (5-fluorouracil, epirubicin, and cyclophosphamide).

Anti-angiogenic agents that may be combined with glycosylated valproic acid and analogs of the present invention include VEGF-TRAP$_5$, anti-VEGF-receptor antibodies, angiostatin, endostatin, batimastat, captopril, cartilage derived inhibitor, genistein, interleukin 12, lavendustin, medroxyprogesterone acetate, recombinant human platelet factor 4, tecogalan, thrombospondin, TNP-470, VEGF antagonists, anti-VEGF monoclonal antibody, soluble VEGF-receptor chimaeric protein, antisense oligonucleotides, antisense oligodexoynucleotides, siRNAs, anti-VEGF aptamers, pigment epithelium derived factor, a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, pentosan polysulfate, a cyclooxygenase inhibitor, carboxyamidotriazole, combretastatin A-4, squalamine, 6-O-chloroacetyl-carbonyl)-fumagillol, thalidomide, troponin-1, indolinethiones, pyridopyrimidines, quinoazolines, phenylpyrrolo-pyriraidines, trastuzumab, bevacizumab, calcium influx inhibitor (CAI), neomycin, squalamme, marimastat, prinomastat (AG-3340), metastat (COL-3) and cinnoline derivatives. Additional anti-angiogenic compounds that may be administered in combination with the compounds of the present invention are described in U.S. Pat. Nos. 5,192,744; 5,426,100; 5,733,876; 5,840,692; 5,854,205; 5,990,280; 5,994,292; 6,342,219; 6,342,221; 6,346,510; 6,479,512; 6,719,540; 6,797,488; 6,849,599; 6,869,952; 6,887,874; 6,958,340 and 6,979,682; each herein incorporated by reference in its entirety.

In some embodiments, the compounds of the present invention are administered in combination with an Hsp90 inhibitor. In some embodiments, Hsp90 inhibitors can be any Hsp90 inhibitor which is used, has been used, or is known to be useful for the treatment of disorders associated with the expression of Hsp90. Examples of Hsp90 inhibitors that may be combined with the compounds of the present invention include geldanamycin, 17-allylamino-17-demethoxygeldanamycin, geldanamycin derivatives such as those described in U.S. Pat. No. 6,890,917 (herein incorporated by reference in its entirety), dexamethasone and benzoquinone ansamycins such as those described in U.S. Pat. No. 6,872,715 (herein incorporated by reference in its entirety). Additional Hsp90 inhibitors are disclosed in U.S. Pat. Nos. 6,613,780; 6,281,229 and 6,903,116; each herein incorporated by reference in its entirety.

Histone deacetylases (HDACs), as that term is used herein, are enzymes that catalyze the removal of acetyl groups from lysine residues in the amino terminal tails of the nucleosomal core histones. As such, HDACs together with histone acetyl transferases (HATs) regulate the acetylation/deacetylation of histones. Histone acetylation/deacetylation affects gene expression and inhibitors of HDACs, such as glycosylated valproic acid and analogs of the present invention may induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs may be inhibited by valproic acid derivatives of the present invention. Class III HDACs form a structurally distant class of NAD dependent enzymes that are related to the yeast SIR2 proteins.

Histone deacetylase inhibitors or HDAC inhibitors, as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes. It is also to be understood that glycosylated valproic acid and analogs of the present invention are capable of inhibiting any of the histone deacetylases set forth above, or any other histone deacetylases.

For example, in patients receiving HDAC inhibitors, the accumulation of acetylated histones in peripheral mononuclear cells as well as in tissue treated with HDAC inhibitors can be determined against a suitable control.

The terms "in combination" and "combined with" refer to the use of more than one treatment. The terms do not restrict the order in which treatments are administered to a subject being treated with the combination, and do not necessarily require that the components be mixed as a mixture. A first treatment can be administered prior to, concurrently with, after, or within any cycling regimen involving the administration of a second treatment to a subject treated with the compounds of the present invention. For example, the first treatment can be administered 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before a treatment; or the first treatment can be administered 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after a second treatment. Such treatments include, for example, the administration of valproic acid derivatives in combination with one or more chemotherapeutic agents or HDAC inhibitors.

The terms "prevent," "preventing," and "prevention," as used herein, refer to a decrease in the occurrence of pathological cells (e.g., a condition associated with the tissue degeneration) in an animal. The prevention may be complete, e.g., the total absence of pathological cells in a subject. The prevention may also be partial, such that the occurrence of pathological cells in a subject is less than that which would have occurred without the present invention.

Certain of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art. Certain of the compounds of the present invention may also exist as diasteroisomers wherein one or more substituents on the valproic acid analog contain one or more chiral centers. It should be recognized that in certain of the compounds, one of the stereoisomers of a valproic acid analog may have a stronger teratogenic effect than the other one and the more teratogenic isomer is thought to inhibit HDACs more efficiently (U.S. Pat. No. 7,265,154; herein incorporated by reference in its entirety). Thus, the present invention encompasses the racemic mixtures of the respective compounds, the less active isomers, and in particular the more active isomers.

Glycosylated valproic acid and analogs according to the present invention are contemplated to be useful in the treatment of patients in both human and veterinary medical practice. Glycosylated valproic acid and analogs can be administered to a patient in need thereof by any of the conventional parenteral routes of administration, as may be appropriate for use in conjunction with the selective activation afforded by glycosylated valproic acid and analogs according to the invention for the disease or condition to be treated. These routes include intravenous (i.v.) injection, intramuscular (i.m.) injection, subcutaneous (s.c.) injection, infusion into a body cavity, cerebrospinal injection, localized infiltration into a target tissue, buccal absorption, and aerosol inhalation, in an amount effective to treat the disease or disorder. Formulations of the compounds of the present invention into pharmaceutical compositions suitable for the chosen route of administration may include any physiologically acceptable solutions, suspensions, emulsions, microemulsions, micellar dispersions, or the like, with any pharmaceutically acceptable excipients, as are known in the art. In addition, formulations may include various encapsulations or depots designed to achieve sustained release of glycosylated valproic acid and analogs, as in those circumstances where a chronic disorder is to be treated.

Compositions comprising glycosylated valproic acid and analogs of the present invention may also be administered by intravenous, intramuscular, topical or oral administration, or by a vascular stent impregnated with a glycosylated valproic acid and analog. While the dosage of therapeutically effective amount of glycosylated valproic acid and analogs of the present invention may vary from, and also depends upon, the age and condition of each individual patient to be treated. When an individual patient is to be treated, in the case of intravenous administration, a daily dose of 0.01-10 mg of glycosylated valproic acid and analogs of the present invention, such as compound of formula I, II, III, IV, V, or VI, or combinations thereof, per kg weight of human being is generally given for treatment. For intramuscular administration, a daily dose of 0.1-10 mg of glycosylated valproic acid and analogs of the present invention, such as compound of formula I, II, III, IV, V, or VI, or combinations thereof, per kg weight of human being, is generally given for treatment. For oral administration, a daily dose of 0.5-50 mg of glycosylated valproic acid and analogs of the present invention, such as compound of formula I, II, III, IV, V, or VI, or combinations thereof, per kg weight of human being, is generally given for treatment.

HDAC inhibitory activity of a particular compound can be determined in vitro using, for example, an enzymatic assay which shows inhibition of at least one histone deacetylase. Further, determination of the accumulation of acetylated histones in cells treated with a particular composition can be determinative of the HDAC inhibitory activity of a compound.

Synthesis of a glycosylated valproic acid derivative typically involves several steps. For example, Scheme 1 may be followed if the synthesis of compounds of formula I in which the sugar group is derived from glucose is desired. Since the ultimate purpose is to esterify the anomeric hydroxy group of the sugar molecule with the carboxylic acid group of the valproic acid derivative, the protection scheme should be such that the group used to protect the anomeric hydroxy group should be removable without affecting the protecting groups of the other hydroxy groups (i.e., hydroxy groups at C-2, C-3, C-4, and C-6). For example, the anomeric hydroxy group of the sugar may be protected using any of the hydroxy protecting groups known to be hydrolyzed under mild acidic conditions. Examples of such protecting groups include 2-methoxyethoxymethyl (MEM) group, 4-pentinyloxymethyl (POM) group, t-butoxymethyl (BOM) group, methoxymethyl (MOM) group, and methylthiomethyl (MTM). Even simple conversion of the anomeric hydroxy group of the sugar to simple ether (e.g., methyl, ethyl, propyl, etc) may be suitable.

In some embodiments, the protecting group can comprise a benzyl group, which can be removed by hydrogenation to yield a valproate analog. In some embodiments, the protecting group can comprise an acetate moiety, such as for example, a halogenated acetate, such as for example, chloroacetate or bromoacetate, or an alkoxyacetate, such as for example, methoxyacetate, ethoxyacetate, propoxyacetate, or the like. These protecting groups can be removed under very mild basic conditions, such as deprotection using sodium carbonate or sodium bicarbonate in methanol, THF and water yielding a valproate analog.

In some embodiments, the anhydride form of valproic acid can be used instead of valproic acid to synthesize the valproate analog.

For each particular protecting group used, there is a known method of attaching the protecting group to and cleaving it from the compound. For example, a sugar protected with a MOM group may be prepared by treating the sugar with methoxymethylene chloride in THF the presence of NaH. Cleavage of the methoxymethyl group of the MOM-protected sugar may be achieved under variety of conditions, for example, reacting the protected sugar with Me$_3$SiBr in dichloromethane at 0° C. for about ten hours is expected to yield almost quantitative de-protected sugar. Further details of protection-deprotection of hydroxy groups may be found in Greene, T. W. and Wuts, E. G. M., "Protective Groups in Organic Synthesis," Wiley & Sons, (2006), Chapter 2; herein incorporated by reference in its entirety.

Scheme 1 shows one approach to the synthesis of glycosylated valproic acid analogs at C-1 of a carbohydrate, with glucose as an example. In this approach, the anomer obtained is β due to the presence and participation of the acyl protecting group at C-2. It should be noted that the acyl protecting groups chosen should be hydrolyzed while leaving the valproate functionality intact. This can be accomplished by employing protecting groups that contain an electron-withdrawing group or groups adjacent to the carbonyl of the ester. In the case shown, that electron group is Cl, to form chloroacetate protecting groups. Other halogens such as Br and I could also be used, as well as dichloro, dihalo, and methoxy, ethoxy, etc. Removal of these protecting groups can be accomplished under very mild conditions such as NaHCO$_3$ in a THF/methanol/water solvent system. After formation of the penta(chloroacetyl) glucose, the requisite C-1 bromide is obtained with hydrobromic acid in acetic acid. Glycosylation with valproic acid to provide predominantly the β anomer can then be accomplished using standard Konigs-Knorr conditions with silver oxide and a silver catalyst, silver triflate. This reaction works best if accompanied with 4 A molecular sieves to absorb the water by-product formed during the reaction. Removal of the protecting groups under the conditions mentioned above should provide the desired β anomer of glucosyl 1-valproate.

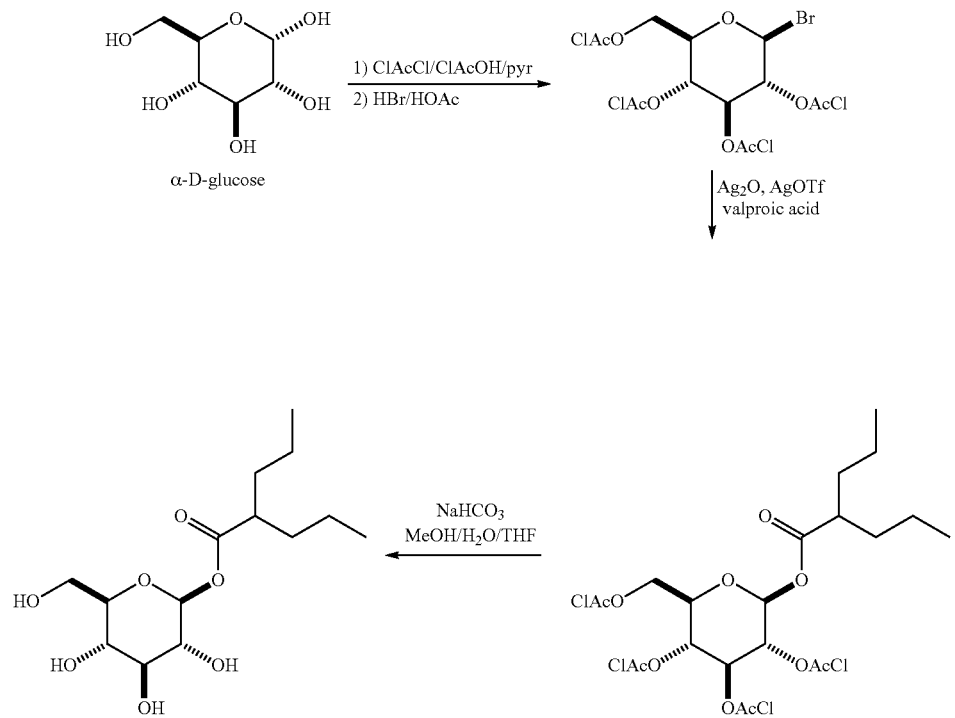

Scheme 1: Synthesis of the β anomer of the glucose analog of valproic acid glycosylated at C-1

Outlined in Scheme 2 is an approach that would provide the corresponding a anomer of that prepared in Scheme 1. In this case, employing ether protecting groups such as benzyl groups eliminates neighboring group participation from the C-2 protecting group. Again, using glucose as an example, known 1-bromo 2,3,4,6-tetra-O-benzyl glucose can be prepared easily be prepared. Glycosylation of valproic acid under Konigs-Knorr conditions using silver oxide and silver triflate as a catalyst should, in this case, provide predominantly the α anomer. Removal of the benzyl groups by hydrogenation under established conditions should provide the desired a anomer of glucosyl 1-valproate.

Scheme 2: Synthesis of the α anomer of the glucose analog of valproic acid glycosylated at C-1

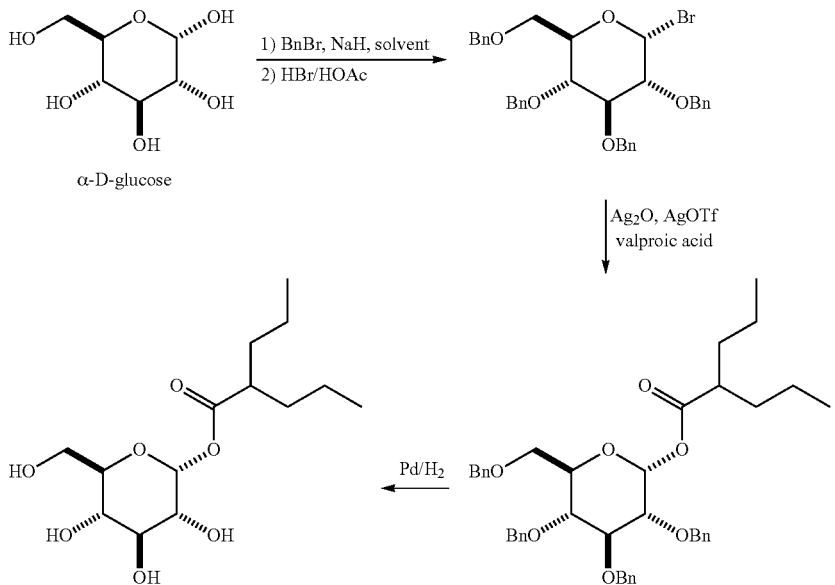

Scheme 3 presents a somewhat different approach in which the anomeric hydroxyl is acylated with valproic acid or related compounds. Also, rather than the more specific pyranose form of glucose presented in Schemes 1 and 2, a general carbohydrate with the furanose form is shown in Scheme 3. It is expected that a variety of different furanose and pyranoses could be substituted for the glucose used in Schemes 1 and 2 and general furanose in Scheme 3. Initially, some or all of the hydroxyl groups in the sugar molecule (for example, a monosaccharide or a disaccharide) is first protected. The hydroxy protecting group may be any protecting group that is suitable. A characteristic property of protecting groups that may be suitable with the process of Scheme 3 is that they are removable under conditions that would leave the other protecting groups intact.

Scheme 3: Synthesis of compounds of formulas I-VI

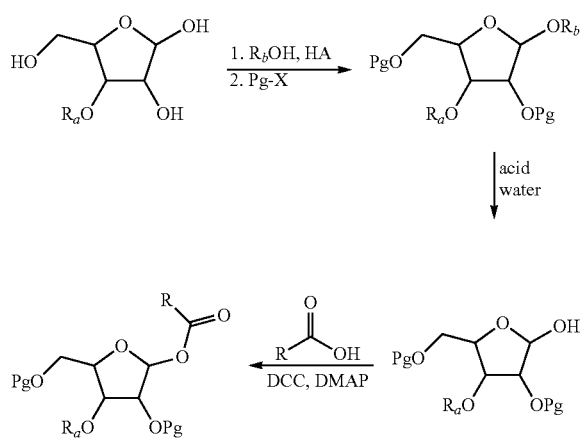

wherein
R is the group

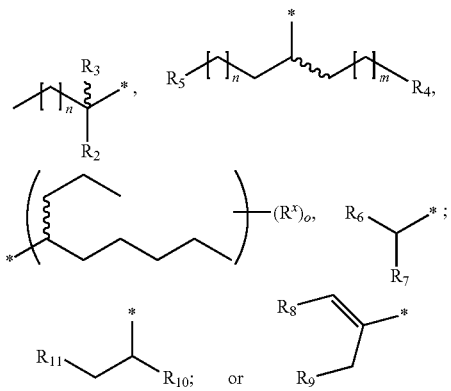

$R_a$ is H or a monomeric or dimeric sugar group;
Pg is a protecting group; $R_bOH$ is an alcohol;
HA is an acid;
DCC is dicyclohecycarboxamide;
DMAP is dimethylaminopyridine;
and the * indicates linkage points.

Scheme 3 can also include a deprotection step to remove the protecting group to yield the compounds of formulas I-VI.

A person skilled in the art would recognize that any exemplified specific reagent in the scheme is merely an example and that it can be replaced with many other reagents. For example, any non-nucleophilic base may be used instead of DMAP. Examples of other non-nucleophilic mild bases that may be suitable with the process of Scheme 1 include pyridine-based bases (such as 2,6-di-tert-butyl-4-methylpyridine and 2,6-di-tert-butylpyridine), tertiary amines (such as ethyldiisopropylamine, triethylamine, and N,N-dimethylcyclohexylamine)) and bicyclic amines (such as 1,4-diazabicyclo[2.2.2]octane (DABCO), 1,4-azabicyclo[2.2.2]octane (ABCO), 1-azabicyclo[3.3.3]undecane (ABCU), 2-azabicyclo[2.2.1]hept-5-en-3-one, 1,3,3-trimethyl-6-azabicyclo[3.2.1]octane, 3-azabicyclo[3.1.0]hexane), 1,5-diazabicyclo9,9-pentamethyl-2,10-diazabicyclo[4.4.0]dec-1-ene, and

[4.3.0]non-5-ene, 1,8-diazabicyclo[5.4.0]undec-7-ene, 3,3,6,6-(dibutylamino)-1,8-diazabicyclo[5.4.0]undec-7-ene).

DCC is an example of carbodiimide that is suitable as a coupling agent for preparing esters and amides from carboxylic acids and alcohols or amines Diisopropylcarbodiimide (DIC) may also be used. Other suitable coupling agents include 1-ethyl-3-(3-dimethylaminopropyl) carbodiimide (EDC), N-cyclohexyl-N'-(2-morpholinoethyl)carbodiimide methyl-p-toluenesulfonate, 1-(3-Dimethylaminopropyl)-3-ethylcarbodiimide, polymer-bound, N-(3-dimethylaminopropyl)-N'-ethylcarbodiimide, N-(3-dimethylaminopropyl)-N'-ethylcarbodiimide hydrochloride, 1,3-di-p-tolylcarbodiimide, and N-Benzyl-N'-cyclohexylcarbodiimide.

Furthermore, in the examples presented above, the valproic acid is attached at the anomeric position, C-1 of the carbohydrate. However, if so desired, valproic acid or its related compounds could be attached at the primary hydroxyl at C-6, as shown in Scheme 4. This might be accomplished directly on the carbohydrate, or it might be necessary to first functionalize the anomeric carbon as an acetal functionality. Selective acylation of the primary C-6 hydroxyl in preference over the secondary hydroxyls with acetyl chloride has been accomplished using a hindered base like collidine or Hunig's base (iPr$_2$EtN) (Ishihar, 1993; Gemma, 2005; each herein incorporated by reference in its entirety). However, with more hindered acid chlorides like the one derived from valproic acid, less hindered bases such as (Kawabata, 2007; Card, 1983; each herein incorporated by reference in its entirety) pyridine with 4-DMAP might prove more successful. Other methods to accomplish the selective acylation also include, but are not limited to, the use of hindered boronic acid catalysts (Lee, 2011; herein incorporated by reference in its entirety), lipases (Bjoerkling, 1989; herein incorporated by reference in its entirety), and per-O-TMS protected monosaccharides (Witschi, 2010; herein incorporated by reference in its entirety).

In some embodiments, the coupling agents comprise a 2,3 dideoxy hexoses, which can be made via the Ferrier reaction following hydrogenation.

The sugar used in Schemes 1, 2 and/or 3 may be any compound having sugar-type structure whether it is naturally occurring or is derived from a naturally occurring sugar. For example, the glycosylated valproic acid analog may be comprised of an analog linked at C-1 of the sugar such as pyranose analogs, furanosse analogs, disaccharide analogs, 2-aminoacyl carbohydrate analogs, 2-deoxy carbohydrate analogs, ribose analogs and 2-deoxyribose analogs as shown, for example, in FIG. 1.

Figure 2:
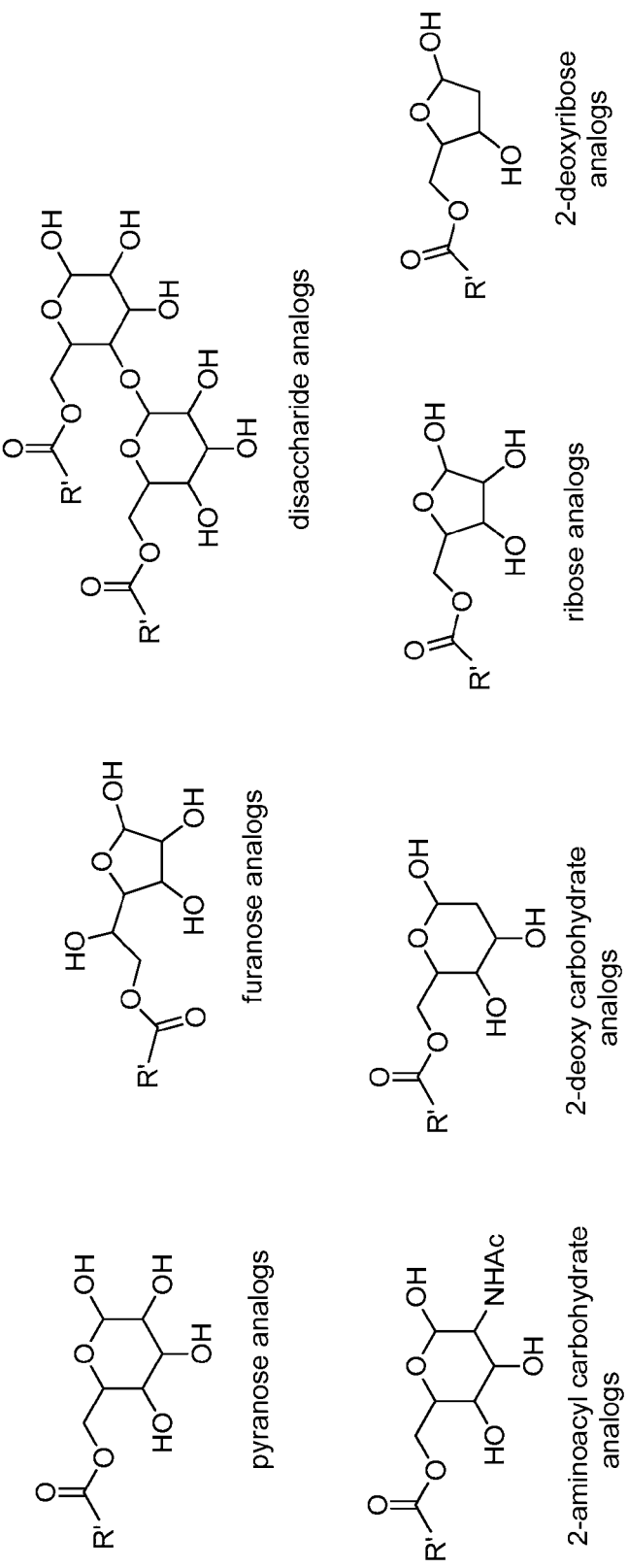
FIG. 2 shows representative glycosylated analogs linked at C-5 or C-6 of the sugar.

The sugar used in Scheme 4 may be any compound having sugar-type structure whether it is naturally occurring or is derived from a naturally occurring sugar. For example, representative glycosylated valproic acid analog may be comprised of an analog linked at C-5 or C-6 of the sugar such as pyranose analogs, furanosse analogs, disaccharide analogs, 2-aminoacyl carbohydrate analogs, 2-deoxy carbohydrate analogs, ribose analogs and 2-deoxyribose analogs as shown, for example, in FIG. 2.

In general, Scheme 4 outlines an approach to forming analogs at C-6, the primary hydroxyl, of the carbohydrate. These analogs functionalized at C-6 may be more stable in a wide variety of formulations and extend release of the valproic acid in vivo as compared to analogs glycosylated at C-1 position.

In addition to direct glycosylation of valproic acid analogs, indirect glycosylation is also contemplated. Insertion of a linker moiety between the saccharide and the valproic acid (or analog thereof) can minimize potential acyl migration of directly linked analogs. In the case of analogs from direct glycosylation, the carbohydrate would be hydrolyzed in vivo by glycosidases. For compounds containing a linker between the saccharide and the valproic acid or analog thereof, glycosidases would leave the linker covalently bound to the valproic acid or analog thereof. Choice of the linker would impact rate of release from the valproic acid or analog thereof.

One example of an extended linker is that of BAY 38-3441 (*Ann. Oncol.*, 2004, 15, 1284-1294; herein incorporated by reference in its entirety). BAY 38-3441 contained a linker Scheme 4: Glycosylation of valproic acid at C-6

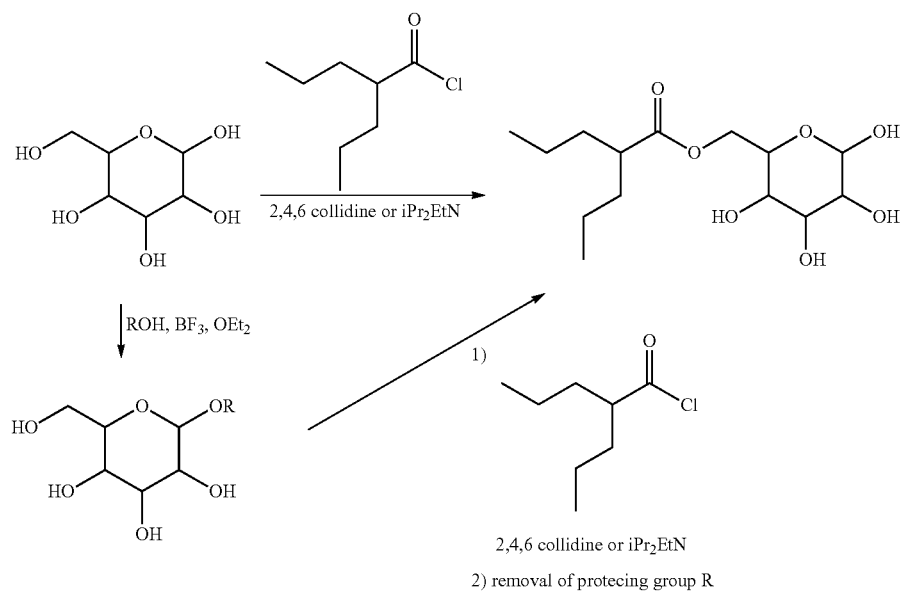

with phenylthiourea joined to a histidine residue, which was used to link a 3-methyl fucose to camptothecin. Clinical failure of BAY 38-3441 was presumed to be due to inadequate camptothecin concentrations in vivo as a result of incomplete release from the parent compound.

Figure 3:
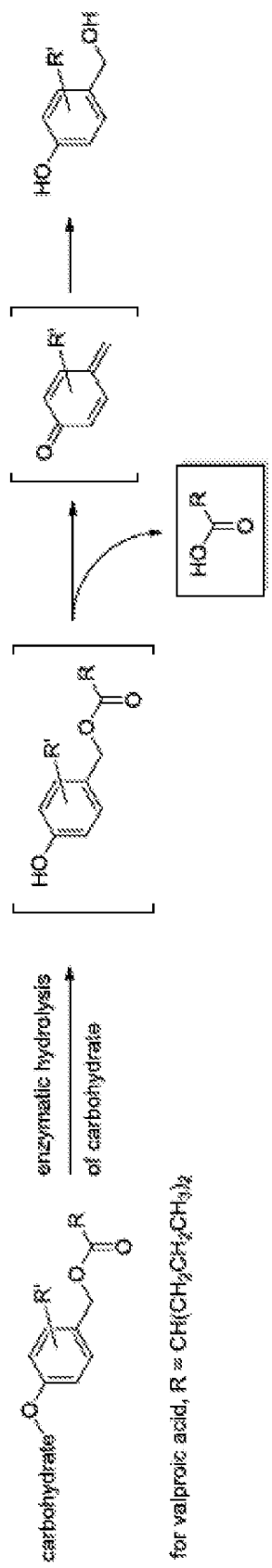
FIG. 3 shows hydrolysis of the glycosyl group from the linker, followed by expulsion of the linker from the valproic acid derivative to provide a free valproic acid.

In the case of the instant invention, it is preferred that upon enzymatic cleavage of the carbohydrate that the linker between the carbohydrate and the valproic acid (or analog thereof) should be quickly expelled. Without being bound by theory, a glycosylated phenol-linked valproic acid (or analog thereof) would undergo hydrolysis to remove the carbohydrate followed by loss of the resultant phenolic benzyl ester (FIG. 3). The half-life of the phenolic benzyl ester intermediate can be modified by substituents on the phenyl ring system (FIG. 3). It is further noted that substitution pattern on the phenyl group can be ortho-, meta- or para-. As shown in FIG. 3, the glycosylated valproic acid derivative can operate as a pro-drug to provide delivery of the valproic acid derivative in vivo. Thus, in some embodiments, the compounds of any of formulas I-VI act as prodrugs to generate a valproic acid or derivative thereof in vivo. In some embodiments, compounds of any of formulas I-VI contain a linker group (designated as Y herein) and act as prodrugs to generate a valproic acid or derivative thereof in vivo. However, operation of the compounds as prodrugs does not require insertion of a linker between the saccharide and the valproic acid derivative. Thus, in some embodiments, compounds of any of formulas I-VI do not contain a linker group (designated as Y herein) and act as prodrugs to generate a valproic acid or derivative thereof in vivo.

Representative preparation of compounds comprising a phenyl or aryl linker is outlined in Scheme 5.

Scheme 5: Preparation of compounds comprising a phenyl linker.

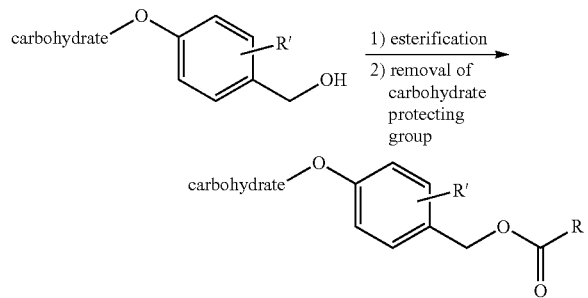

Following etherification of a protected carbohydrate with a phenol derivative such as a protected 4-hydroxyalkyl phenol and subsequent removal of the protecting group would provide the carbohydrate attached to the phenol linker. Esterification of the primary alcohol with an acid derivative would occur under conditions known to the skilled artisan to append the valproic acid or analog thereof. Removal of the carbohydrate protecting groups would provide the glycosylated valproic acid analog containing a linker between the sugar and the valproic acid or analog thereof.

Having now fully described this invention, it will be understood by those of ordinary skill in the art that the same can be performed within a wide and equivalent range of conditions, formulations, and other parameters without affecting the scope of the invention or any embodiment thereof. All patents, patent applications and publications cited herein are fully incorporated by reference herein in their entireties.

REFERENCES

Ishihar, K. et al (1993) An Extremely Simple, Convenient, and Selective Method for Acetylating Primary Alcohols in the Presence of Secondary Alcohols, *J. Org. Chem.*, 58, 3791-3793.

Kawabata, T. et al (2007) A Catalytic One-Step Process for the Chemo- and Regioselective Acylation of Monosaccharides, *J. Am. Chem. Soc.* 129, 12890-12895.

Card, P. J. et al (1983) Fluorinated carbohydrates. 2. Selective fluorination of gluco- and mannopyranosides. Use of 2-D NMR for structural assignments, *J. Org. Chem.* 48, 4734-4743.

Gemma, E. et al. (2005) Synthesis of the tetrasaccharide α-d-Glcp-(1-3)-α-d-Manp-(1-2)-α-d-Manp-(1-2)-α-d-Manp recognized by Calreticulin/Calnexin, *Carbohydr. Res.* 340, 2558-2562.

Lee, D.; Tayklor, M. S. (2011) Boronic Acid-Catalyzed Regioselective Acylation of Carbohydrate Derivatives, *J. Am. Chem. Soc.*, 133, 3724-3727.

Witschi, M. A. and Gervay-Hague, J. (2010) Selective Acetylation of per-O-TMS-Protected Monosaccharides, *Org. Lett.*, 12(19), 4312-4315.

Bjoerkling, F. et al (1989) *J. Chem. Soc., Chem. Comm.* 934-935.

It will recognized that one or more features of any embodiments disclosed herein may be combined and/or rearranged within the scope of the invention to produce further embodiments that are also within the scope of the invention.

Those skilled in the art will recognize, or be able to ascertain, using no more than routine experimentation, numerous equivalents to the specific substances and procedures described herein. Such equivalents are considered to be within the scope of this invention, and are covered by the following claims.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Synthesis of the β Anomer of the Glucose Analog of Valproic Acid Glycosylated at C-1

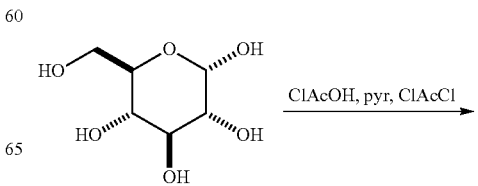

-continued

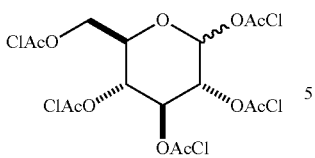

Glucose can be suspended in a combination of 8 equivalents each of chloroacetic acid and pyridine. Chloroacetyl chloride (6 equivalents) can then be added slowly and the progress of the reaction monitored by HPLC, LC-MS or TLC. Once the reaction is complete, the contents can then be poured into solvent (ether, ethyl acetate or dichloromethane) of 10 times its volume, and the resulting organic layer washed successively with an equal volume of water, saturated sodium bicarbonate, dilute (5%) HCl, saturated $CuSO_4$, and brine. The solvent can then be removed under reduced pressure and the resulting syrup purified by flash silica gel column chromatography to provide the product 1,2,3,4,6-penta(chloroacetyl) glucose as a mix of anomers.

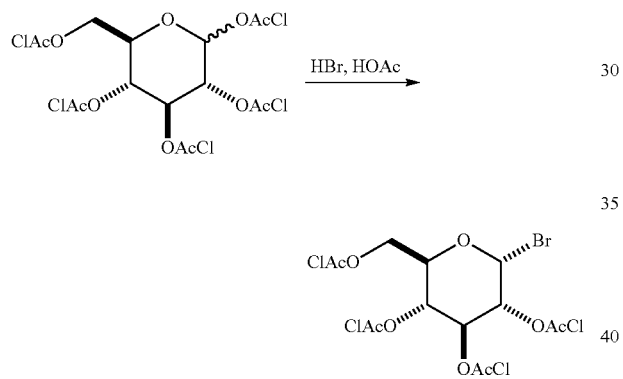

1,2,3,4,6-Penta(chloroacetyl)glucose can then be dissolved in 32-35% HBr in acetic acid such that 5-6 equivalents of HBr are present in the reaction mixture. The reaction mixture can be stirred and monitored by HPLC, LC-MS or TLC until complete. The mixture would then poured into 5 times its volume of dichloromethane and the mixture washed 3 times with an equal volume of water and once each of an equal volume of saturated $NaHCO_3$ and brine in that order. The solvent would be removed under reduced pressure and the product purified by silica gel column chromatography if needed to provide α-2,3,4,6-Tetra(chloroacetyl) 1-bromoglucose. It should be noted that some of the Cl atoms on the chloroacetates might be displaced by Br; this impurity would not affect the final product.

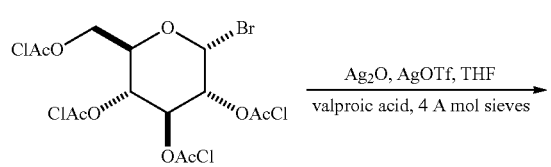

-continued

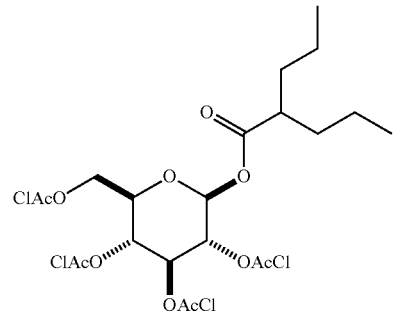

α-2,3,4,6-Tetra(chloroacetyl) 1-bromoglucose would then be dissolved in an appropriate solvent (THF) and dried crushed 4 A molecular sieves added. Then more than 1 equivalent of both valproic acid and $Ag_2O$ added with a catalytic amount of AgOTf. The reaction would be monitored by HPLC, LC-MS or TLC until progress ceases or is complete. The reaction mixture would then be filtered, the solvent removed and the product β-2,3,4,6-tetra(chloroacetyl)-1-valproylglucose.

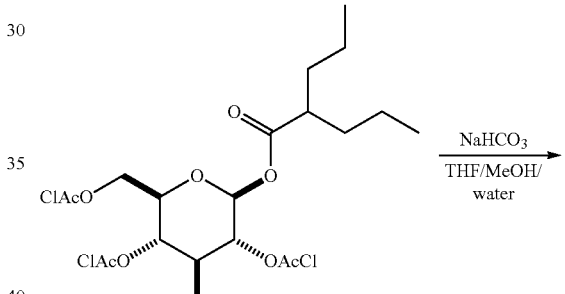

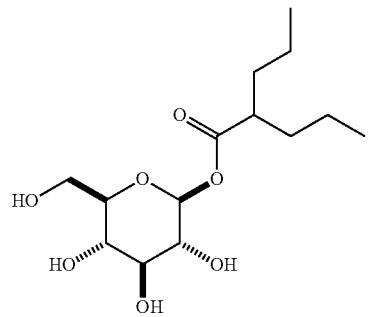

β-2,3,4,6-tetra(chloroacetyl)-1-valproylglucose would then be dissolved in a 1:1:1 mixture of methanol/THF/water and 6 equivalents of ground $NaHCO_3$ added. The reaction mixture would then be stirred and progress monitored by HPLC, LC-MS or TLC. When the reaction is complete and all of the chloroacetates hydrolyzed, the solvent would be removed under reduced pressure and the product β-1-valproylglucose purified by silica gel column chromatography.

Example 2

Alternative Synthesis of the β Anomer of the Glucose Analog of Valproic Acid Glycosylated at C-1

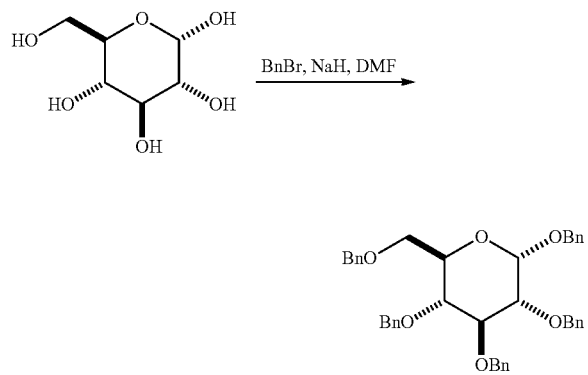 [SMILES: OC[C@H]1O[C@H](O)[C@H](O)[C@@H](O)[C@@H]1O ; c1ccc(COC[C@H]2O[C@H](OCc3ccccc3)[C@H](OCc3ccccc3)[C@@H](OCc3ccccc3)[C@@H]2OCc2ccccc2)cc1]

α-Glucose would be dissolved or suspended in a minimum amount of an appropriate solvent (DMF) and 6 equivalents of benzyl bromide added. Then 6 equivalents of a base such as sodium hydride would be added in small portions such that the temperature of the reaction mixture does not exceed approximately 60° C. After all of the base is added, the reaction mixture is monitored by HPLC, LC-MS or TLC. Once the reaction ceases to proceed further or is complete, it is poured into approximately 10 times its volume of dichloromethane. This mixture would then be washed successively with equal volume water, saturated NHCO$_3$ and brine. The solvent would then be removed under reduced pressure, and silica gel column chromatography would provide the product α-1,2,3,4,6-penta-O-benzylglucose.

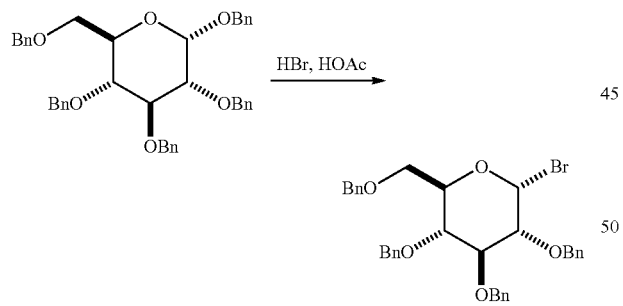

α-1,2,3,4,6-Penta-O-benzyl glucose would then be dissolved in 32-35% HBr in acetic acid such that there are 5 equivalents of HBr present and the mixture stirred and monitored by HPLC, LC-MS or TLC until complete. The reaction mixture would then be poured into dicholormethane 5 times its volume and washed three times with an equal volume of water, once with an equal volume of saturated NaHCO$_3$, and once with brine. The solvent would be removed under reduced pressure and the resultant oil purified by silica gel column chromatography to provide the product α-2,3,4,6-tetra-O-benzyl-1-bromoglucose.

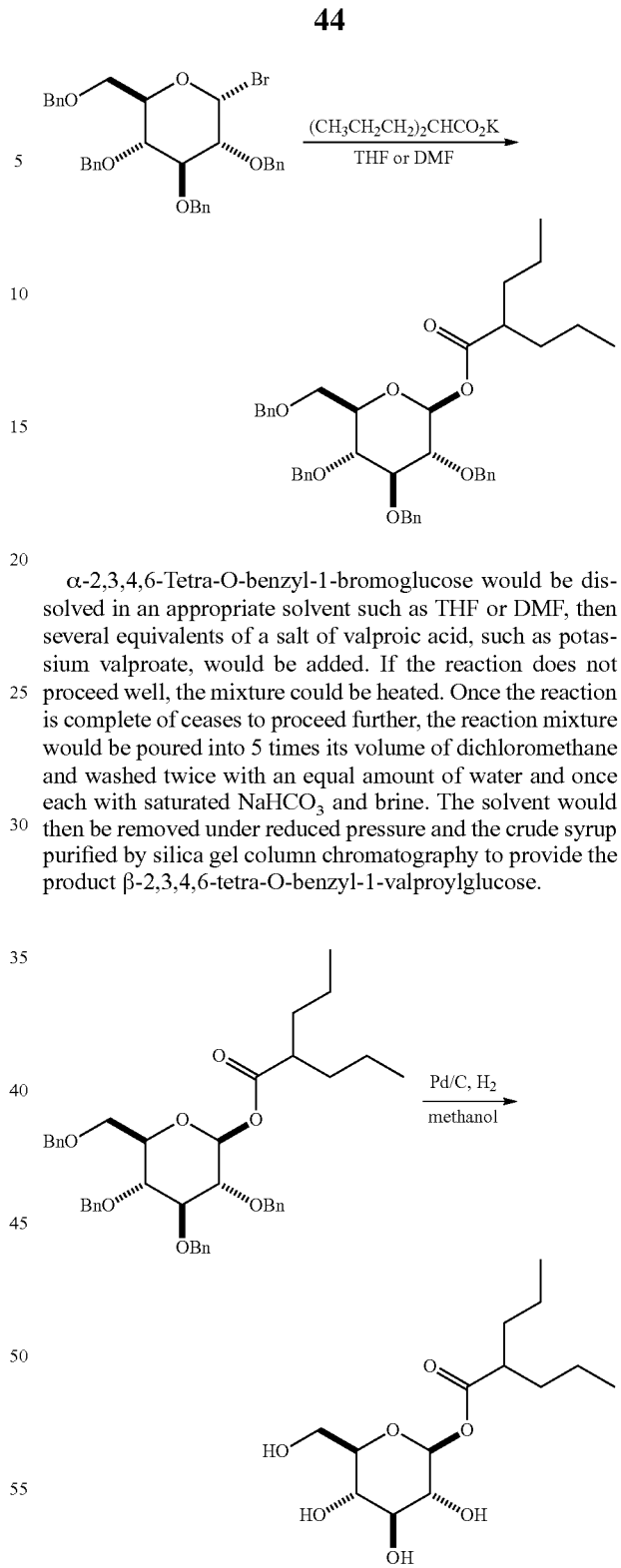

α-2,3,4,6-Tetra-O-benzyl-1-bromoglucose would be dissolved in an appropriate solvent such as THF or DMF, then several equivalents of a salt of valproic acid, such as potassium valproate, would be added. If the reaction does not proceed well, the mixture could be heated. Once the reaction is complete of ceases to proceed further, the reaction mixture would be poured into 5 times its volume of dichloromethane and washed twice with an equal amount of water and once each with saturated NaHCO$_3$ and brine. The solvent would then be removed under reduced pressure and the crude syrup purified by silica gel column chromatography to provide the product β-2,3,4,6-tetra-O-benzyl-1-valproylglucose.

β-2,3,4,6-Tetra-O-benzyl-1-valproylglucose would be dissolved in a minimum amount of an appropriate solvent such as methanol, toluene, or THF, a catalytic amount of Pd on carbon added. The gas space in the reaction vessel would then be replaced with a neutral one (such as nitrogen), then replaced with hydrogen at a slightly positive pressure. This pressure would be maintained and the reaction would be monitored by HPLC, LC-MS or TLC. After completion of the reaction, the hydrogen would be removed by vacuum, replaced with a neutral (nitrogen) atmosphere before exposing to air. The reaction would be filtered and the solvent removed under reduced pressure. The crude syrup would then be purified by silica gel column chromatography to provide the product β-1-valproylglucose.

Example 3

Synthesis of the α Anomer of the Glucose Analog of Valproic Acid Glycosylated at C-1

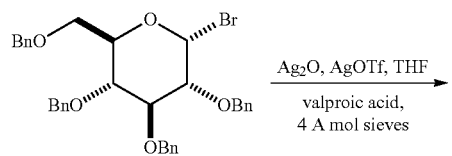

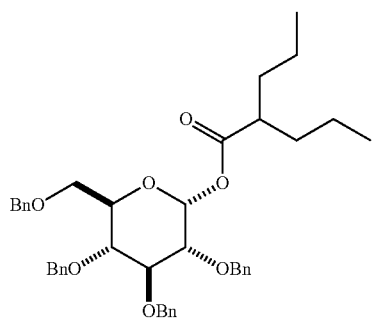

α-2,3,4,6-Tetra-O-benzyl 1-bromoglucose (see Examples 1 and 2) would be dissolved in an appropriate solvent (THF) and dried crushed 4 A molecular sieves added. Then more than 1 equivalent of both valproic acid and Ag$_2$O can then be added with a catalytic amount of AgOTf. The reaction would be monitored by HPLC, LC-MS or TLC until progress ceases or is complete. The reaction mixture would then be filtered, the solvent removed and the product α-2,3,4,6-tetra-O-benzyl-1-valproylglucose.

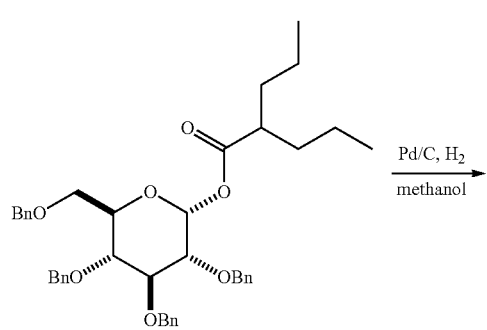

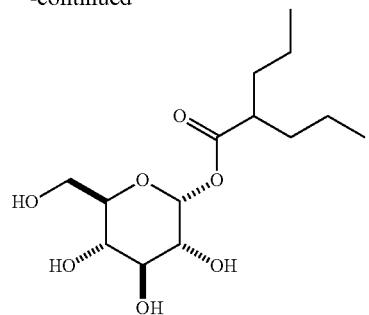

α-2,3,4,6-Tetra-O-benzyl-1-valproylglucose would be dissolved in a minimum amount of an appropriate solvent such as methanol, toluene, or THF, a catalytic amount of Pd on carbon added. The gas space in the reaction vessel would then be replaced with a neutral one (such as nitrogen), then replaced with hydrogen at a slightly positive pressure. This pressure would be maintained and the reaction would be monitored by HPLC, LC-MS or TLC. After completion of the reaction, the hydrogen would be removed by vacuum, replaced with a neutral (nitrogen) atmosphere before exposing to air. The reaction would be filtered and the solvent removed under reduced pressure. The crude syrup would then be purified by silica gel column chromatography to provide the product α-1-valproylglucose.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways to obtain additional embodiments within the scope and spirit of the invention.

What is claimed:
1. A compound of formula IV or V:

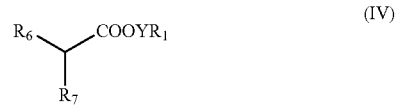

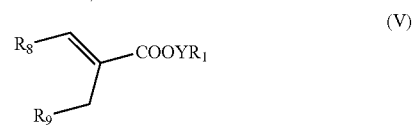

wherein
R$_1$ is a naturally occurring saccharide linked at the anomeric carbon of the saccharide, provided R1 is not glucuronate;
each of R$_6$ and R$_7$ is independently a linear or branched, saturated or partially unsaturated aliphatic C$_2$-C$_{20}$ hydrocarbon chain;
each of R$_8$ and R$_9$ is independently a linear or branched aliphatic C$_2$-C$_{20}$ hydrocarbon chain which is optionally substituted with a C$_3$-C$_9$ aliphatic or aromatic cyclohydrocarbon or heterocyclic group or having 1-3 substituents independently selected from the group consisting of halogen atoms, amino, hydroxy, carboxylic acid group, ester, amide, and cyano wherein one or more of the hydroxy, carboxylic acid, amine, or amide group is optionally glycosylated with a saccharide group; and Y is a bond or —$CH_2$-aryl-O—, wherein the aryl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —$NH_2$, —$NO_2$, and —CN;

or a pharmaceutically acceptable salt thereof, wherein the compound is predominantly an individual anomer.

2. The compound of claim 1, wherein $R_1$ is glucoside, mannoside, or galactoside.

3. The compound of claim 1, wherein each of $R_6$ and $R_7$ is independently a linear or branched, saturated aliphatic $C_2$-$C_{10}$ hydrocarbon chain;

each of $R_8$ and $R_9$ is independently a linear or branched aliphatic $C_2$-$C_{10}$ hydrocarbon chain, optionally having 1-3 substituents independently selected from the group consisting of halogen atoms, amino, hydroxy, carboxylic acid group, ester, and amide; and Y is a bond or —$CH_2$-aryl-O—, wherein the aryl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —$NH_2$, —$NO_2$, and —CN.

4. The compound of claim 1, wherein each of $R_6$ and $R_7$ is independently a linear or branched, saturated aliphatic $C_2$-$C_{10}$ hydrocarbon chain;

each of $R_8$ and $R_9$ is independently a linear or branched aliphatic $C_2$-$C_{10}$ hydrocarbon chain, optionally having 1-3 substituents independently selected from the group consisting of halogen atoms, amino, and hydroxyl; and Y is a bond or —$CH_2$-phenyl-O—, wherein the phenyl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —$NH_2$, —$NO_2$, and —CN.

5. The compound of claim 1, wherein $R_1$ is glucoside, mannoside, galactoside, alloside, guloside, idoside, taloside, rhamnoside, maltoside, or lactoside;

each of $R_6$ and $R_7$ is independently a linear or branched, saturated aliphatic $C_2$-$C_6$ hydrocarbon chain;

each of $R_8$ and $R_9$ is independently a linear or branched aliphatic $C_2$-$C_6$ hydrocarbon chain; and Y is a bond,

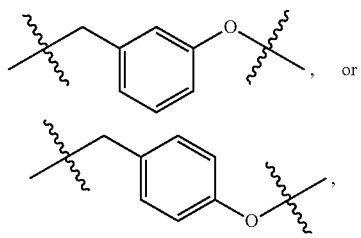

wherein the phenyl group is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_1$-$C_6$ thioalkyl, —N($C_1$-$C_3$ alkyl)($C_1$-$C_3$ alkyl), —NH($C_1$-$C_3$ alkyl), —$NH_2$, —$NO_2$, and —CN.

6. The compound of claim 1, wherein $R_1$ is a monosaccharide, disaccharide, or trisaccharide.

7. The compound of claim 1, wherein $R_1$ is a furanose or a pyranose.

8. The compound of claim 1, wherein $R_1$ is glucoside, mannoside, galactoside, alloside, guloside, idoside, taloside, rhamnoside, maltoside, lactoside, glucosamine, galactosamine, mannosamine, N-acetylglucosamine, N-acetylgalactosamine, or N-acetylmannosamine.

9. The compound of claim 1 wherein the anomeric carbon is at the C-1 position of the saccharide.

10. A compound selected from the group consisting of β-1-valproylglucose and α-1-valproylglucose, wherein the compound is predominantly an individual anomer.

* * * * *